United States Patent
Tramm et al.

(10) Patent No.: US 10,827,948 B1
(45) Date of Patent: Nov. 10, 2020

(54) METHOD AND APPARATUS FOR MULTI-PART CLOSE FITTING HEAD COIL

(71) Applicant: Life Services LLC, Minneapolis, MN (US)

(72) Inventors: Brandon J. Tramm, Maple Grove, MN (US); Charles A. Lemaire, Apple Valley, MN (US); Matthew T. Waks, Coon Rapids, MN (US); Scott M. Schillak, Minneapolis, MN (US)

(73) Assignee: Life Services, LLC, Minneapolis, MN (US)

( * ) Notice: Subject to any disclaimer, the term of this patent is extended or adjusted under 35 U.S.C. 154(b) by 147 days.

(21) Appl. No.: 15/361,364

(22) Filed: Nov. 25, 2016

Related U.S. Application Data

(60) Provisional application No. 62/260,236, filed on Nov. 25, 2015.

(51) Int. Cl.
*A61B 5/055* (2006.01)
*A61B 5/00* (2006.01)
(Continued)

(52) U.S. Cl.
CPC .......... *A61B 5/0555* (2013.01); *A61B 5/0042* (2013.01); *A61B 5/7405* (2013.01);
(Continued)

(58) Field of Classification Search
CPC ....... A61B 5/00; A61B 5/0555; A61B 5/0042; A61B 5/7405; G01R 33/00; G01R 33/34; G01R 33/341; G01R 33/3614
See application file for complete search history.

(56) References Cited

U.S. PATENT DOCUMENTS

| 4,682,125 A | 7/1987 | Harrison et al. |
| 4,763,076 A | 8/1988 | Arakawa et al. |

(Continued)

FOREIGN PATENT DOCUMENTS

WO   WO_2000037918   6/2000

OTHER PUBLICATIONS

Roemer et al., "Magnetic Resonance in Medicine", vol. 16, pp. 192-225 (1990), entitled The NMR Phased Array. (Year: 1990).*

(Continued)

*Primary Examiner* — Pascal M Bui Pho
*Assistant Examiner* — Sean D Mattson
(74) *Attorney, Agent, or Firm* — Charles A. Lemaire; Jonathan M. Rixen; Lemaire Patent Law Firm, P.L.L.C.

(57) ABSTRACT

A method and apparatus for receiving (RX) radio-frequency (RF) signals suitable for MRI and/or MRS from a plurality of MRI "coil loops" in each of a plurality of coil parts, each coil part having a subset of the total number of coil loops. In some embodiments, a first base part, optionally having no coils, is used to provide support of the plurality of coil parts, wherein the plurality of coil parts include a second part holding back-of-the-head coil loops, a third part holding right-side-of-the-head coil loops, a fourth part holding right-side-of-the-head coil loops, and a fifth part holding top-of-the-head coil loops. In some embodiments, the system provides for repeatable positioning, frequency tuning, and impedance matching such that experimental conditions can be replicated for later examinations of each of a plurality of patients having differing impacts on positioning, tuning and matching of the various coil parts.

20 Claims, 26 Drawing Sheets

(51) Int. Cl.
   *G01R 33/36* (2006.01)
   *G01R 33/341* (2006.01)
   *G01R 33/34* (2006.01)

(52) U.S. Cl.
   CPC ............ *G01R 33/34* (2013.01); *G01R 33/341* (2013.01); *G01R 33/3614* (2013.01)

(56) References Cited

U.S. PATENT DOCUMENTS

| | | | |
|---|---|---|---|
| 4,801,553 A | 1/1989 | Owen et al. | |
| 4,885,539 A | 12/1989 | Roemer et al. | |
| 4,894,589 A | 1/1990 | Borowiec | |
| 4,947,119 A | 8/1990 | Ugurbil et al. | |
| 5,007,425 A * | 4/1991 | Vanek | A61B 5/0555 600/415 |
| 5,075,600 A | 12/1991 | El-Hamasy et al. | |
| 5,150,710 A * | 9/1992 | Hall | G01R 33/28 324/318 |
| 5,304,930 A | 4/1994 | Crowley et al. | |
| 5,343,580 A * | 9/1994 | Bonutti | A61B 5/0555 378/208 |
| 5,480,482 A | 1/1996 | Novinson | |
| 5,548,218 A * | 8/1996 | Lu | G01R 33/34 324/318 |
| 5,557,247 A | 9/1996 | Vaughn, Jr. | |
| 5,665,398 A | 9/1997 | McCormick | |
| 5,714,831 A | 2/1998 | Walker et al. | |
| 5,744,957 A | 4/1998 | Vaughan, Jr. | |
| 5,836,877 A | 11/1998 | Zavislan | |
| 5,886,596 A | 3/1999 | Vaughan, Jr. | |
| 5,908,386 A | 6/1999 | Ugurbil et al. | |
| 5,990,681 A | 11/1999 | Richard et al. | |
| 6,002,251 A | 12/1999 | Sun | |
| 6,079,681 A * | 6/2000 | Stern | G01R 33/34007 248/278.1 |
| 6,100,694 A | 8/2000 | Wong | |
| 6,150,816 A | 11/2000 | Srinivasan | |
| 6,300,761 B1 | 10/2001 | Hagen et al. | |
| 6,396,271 B1 | 5/2002 | Burl et al. | |
| 6,495,069 B1 | 12/2002 | Lussey et al. | |
| 6,534,983 B1 | 3/2003 | Boskamp et al. | |
| 6,538,441 B1 | 3/2003 | Watkins et al. | |
| 6,593,744 B2 | 7/2003 | Burl et al. | |
| 6,605,775 B1 | 8/2003 | Seeber et al. | |
| 6,633,161 B1 | 10/2003 | Vaughan, Jr. | |
| 6,636,037 B1 | 10/2003 | Ou-Yang | |
| 6,636,414 B2 | 10/2003 | Obert et al. | |
| 6,650,116 B2 | 11/2003 | Garwood et al. | |
| 6,664,465 B2 | 12/2003 | Seeber et al. | |
| 6,788,056 B2 | 9/2004 | Vaughan, Jr. et al. | |
| 6,788,057 B1 | 9/2004 | Petropoulos et al. | |
| 6,788,058 B1 | 9/2004 | Petropoulos et al. | |
| 6,822,448 B2 | 11/2004 | Watkins et al. | |
| 6,822,450 B2 | 11/2004 | Klinge et al. | |
| 6,834,238 B1 | 12/2004 | Hochman | |
| 6,888,348 B2 | 5/2005 | Kupce | |
| 6,930,480 B1 | 8/2005 | Fujita et al. | |
| 6,946,840 B1 | 9/2005 | Zou et al. | |
| 6,958,607 B2 | 10/2005 | Vaughan, Jr. et al. | |
| 6,969,992 B2 | 11/2005 | Vaughan, Jr. et al. | |
| 6,975,115 B1 | 12/2005 | Fujita et al. | |
| 6,977,502 B1 | 12/2005 | Hertz | |
| 6,980,002 B1 | 12/2005 | Petropoulos et al. | |
| 7,023,209 B2 | 4/2006 | Zhang et al. | |
| 7,042,222 B2 | 5/2006 | Zheng et al. | |
| 7,071,693 B2 | 7/2006 | Yasuhara | |
| 7,084,631 B2 | 8/2006 | Qu et al. | |
| 7,088,104 B2 | 8/2006 | Bottomley | |
| 7,119,541 B2 | 10/2006 | Barberi | |
| 7,123,012 B2 | 10/2006 | Srinivasan | |
| 7,268,554 B2 | 9/2007 | Vaughan, Jr. | |
| 7,279,899 B2 | 10/2007 | Michaeli et al. | |
| 7,292,038 B2 | 11/2007 | Doty | |
| 7,295,870 B2 | 11/2007 | Allain et al. | |
| 7,403,006 B2 | 7/2008 | Garwood et al. | |
| 7,436,103 B2 | 10/2008 | Kawakubo et al. | |
| 7,439,736 B2 | 10/2008 | Meaney et al. | |
| 7,474,098 B2 | 1/2009 | King | |
| 7,514,926 B2 | 4/2009 | Adriany et al. | |
| 7,526,330 B1 * | 4/2009 | Randell | A61B 5/055 324/309 |
| 7,598,739 B2 | 10/2009 | Vaughan, Jr. et al. | |
| 7,633,293 B2 | 12/2009 | Olson et al. | |
| 7,672,650 B2 | 3/2010 | Sorrells et al. | |
| 7,710,117 B2 | 5/2010 | Vaughan et al. | |
| 7,777,484 B2 | 8/2010 | Garwood et al. | |
| 7,800,368 B2 | 9/2010 | Vaughan et al. | |
| 8,035,384 B2 | 10/2011 | Saha | |
| 8,093,900 B2 | 1/2012 | Bennett | |
| 8,093,978 B2 | 1/2012 | Kawarai et al. | |
| 8,193,809 B2 | 6/2012 | Akgun et al. | |
| 8,217,653 B2 | 7/2012 | Vaughan et al. | |
| 8,222,796 B2 | 7/2012 | Bhaskaran et al. | |
| 8,299,681 B2 | 10/2012 | Snyder et al. | |
| 8,380,266 B2 | 2/2013 | Vaughan, Jr. et al. | |
| 8,604,791 B2 | 12/2013 | Vaughan | |
| 8,674,695 B2 | 3/2014 | Wiggins | |
| 8,788,044 B2 | 7/2014 | John | |
| 8,854,042 B2 | 10/2014 | Vaughan et al. | |
| 9,097,769 B2 | 8/2015 | Schillak et al. | |
| 9,160,295 B2 | 10/2015 | Waks et al. | |
| 9,320,452 B2 | 4/2016 | Garwood et al. | |
| 2003/0091980 A1 | 5/2003 | Lynch et al. | |
| 2003/0206019 A1 | 11/2003 | Boskamp | |
| 2004/0092809 A1 * | 5/2004 | DeCharms | G01R 33/4806 600/410 |
| 2004/0193038 A1 * | 9/2004 | Reykowski | G01R 33/54 600/410 |
| 2005/0107686 A1 * | 5/2005 | Chan | G01R 33/3415 600/422 |
| 2005/0264291 A1 | 12/2005 | Vaughan et al. | |
| 2006/0001426 A1 | 1/2006 | Vaughan et al. | |
| 2006/0279284 A1 | 12/2006 | Vaughan, Jr. | |
| 2007/0161891 A1 * | 7/2007 | Moore | A61B 5/055 600/421 |
| 2007/0191706 A1 * | 8/2007 | Calderon | A61G 7/1034 600/415 |
| 2007/0236490 A1 | 10/2007 | Casteele et al. | |
| 2008/0007259 A1 * | 1/2008 | Driemel | G01R 33/3415 324/260 |
| 2008/0180101 A1 | 7/2008 | Bradshaw et al. | |
| 2008/0238424 A1 * | 10/2008 | Possanzini | G01R 33/341 324/318 |
| 2009/0088627 A1 * | 4/2009 | Piferi | A61B 5/055 600/422 |
| 2009/0134965 A1 | 5/2009 | Lemdiasov et al. | |
| 2009/0264733 A1 | 10/2009 | Corum et al. | |
| 2013/0106416 A1 | 5/2013 | Morich et al. | |
| 2013/0131498 A1 * | 5/2013 | Taracila | G01R 33/34084 600/422 |
| 2013/0317346 A1 * | 11/2013 | Alagappan | G01R 33/34046 600/415 |
| 2014/0300360 A1 * | 10/2014 | Lin | G01R 33/3415 324/318 |
| 2015/0196226 A1 | 7/2015 | Tramm et al. | |
| 2015/0323624 A1 | 11/2015 | Feinberg et al. | |

OTHER PUBLICATIONS

Augustine, George J., "Combining patch-clamp and optical methods in brain slices", "Journal of Neuroscience Methods", Oct. 1994, pp. 163-169, vol. 54, Publisher: Elsevier.

Cho, Y.K., et al., "Noninvasive measurements of transmural myocardial metabolites using 3-D (31)P NMR spectroscopy.", "Am J Physiology", Jan. 2001, pp. H489-H497, vol. 280, No. 1.

Nelder, J.A., et al., "A simplex method for function minimization", "Comput J.", 1965, pp. 308-313, vol. 7, No. 4.

Roemer, et al., "The NMR Phased Array", "Magnetic Resonance in Medicine", Nov. 1990, pp. 192-225, vol. 16, No. 2.

(56) References Cited

OTHER PUBLICATIONS

Sung K., et al., "B1+ Compensation in 3T Cardiac imaging Using Short 2DRF Pulses", "Magnetic Resonance in Medicine ", Mar. 2008, pp. 441-446, vol. 59, No. 3.

Vaughan, J.T., et al., "Clinical Imaging at 7T with a 16 Channel Whole Body Coil and 32 Receive Channels.", "Proceedings 17th Scientific Meeting, International Society for Magnetic Resonance in Medicine", Apr. 2009, p. 392.

Wiggins, et al., "96-Channel Receive-Only Head Coil for 3 Tesla: Design Optimization and Evaluation", "Magn. Reson. Med.", Sep. 2009, pp. 754-762, vol. 62, No. 3.

* cited by examiner

FIG. 12   BOTTOM PIECE (120) CAN BE REMOVED AND REPLACED WITH A "DUMMY" (COILLESS) HOUSING

METHOD AND APPARATUS FOR MULTI-PART CLOSE FITTING HEAD COIL

CROSS-REFERENCE TO RELATED APPLICATIONS

This application claims priority benefit, under 35 U.S.C. § 119(e), of U.S. Provisional Patent Application No. 62/260,236 filed Nov. 25, 2015 by Brandon J. Tramm et al., titled "Method and apparatus for multi-part close-fitting head coil," which is incorporated herein by reference in its entirety.

This application is related to:

U.S. Provisional Patent Application No. 61/906,409 filed Nov. 19, 2013 by Brandon J. Tramm, titled "Method and apparatus for adjustable earpieces in an MRI system,"

U.S. patent application Ser. No. 14/538,635 filed Nov. 11, 2014 by Brandon J. Tramm, titled "Method and apparatus for adjustable earpieces in an MRI system" (which issued as U.S. Pat. No. 9,700,232 on Jul. 11, 2017), U.S. patent application Ser. No. 14/548,276 filed Nov. 19, 2014 by Brandon J. Tramm et al., titled "Method and positionable patient-interface apparatus for an MRI system" (which issued as U.S. Pat. No. 9,820,676 on Nov. 21, 2017), and U.S. patent application Ser. No. 15/143,498 filed Apr. 29, 2016 by Scott M. Schillak titled "Device and method for simultaneous TX/RX in strongly coupled MRI coil loops" (which issued as U.S. Pat. No. 10,288,711 on May 14, 2019), each of which is incorporated herein by reference in its entirety.

FIELD OF THE INVENTION

This invention relates to the field of magnetic-resonance imaging (MRI) and magnetic-resonance spectroscopy (MRS), and more specifically to a method and apparatus for transmitting (TX) and receiving (RX) radio-frequency (RF) signals suitable for MRI and/or MRS from MRI "coil loops" (antennae), each contained in one or a plurality of head-coils parts, wherein the coil loops that are overlapped and/or concentric, but optionally sized differently and/or located at different elevations (distances from the patient's tissue) in order to extract signal from otherwise cross-coupled coil loops and to improve signal-to-noise ratio (SNR) of the received signal.

BACKGROUND OF THE INVENTION

U.S. Pat. No. 6,605,775 to Seeber et al. issued Aug. 12, 2003 with the title "Floating radio frequency trap for shield currents" and is incorporated herein by reference. In U.S. Pat. No. 6,605,775, Seeber et al. describe a floating shield current trap that provides first and second concentric tubular conductors electrically connected to provide a resonance-induced high impedance of current flow in a path consisting of the inner and outer conductors and their junctions thereby suppressing coupled current flow on a shield of a conductor contained within the first inner tubular conductor.

U.S. Pat. No. 6,664,465 to Seeber issued Dec. 16, 2003 with the title "Tuning system for floating radio frequency trap" and is incorporated herein by reference. In U.S. Pat. No. 6,664,465, Seeber describes a floating shield current trap provides two resonance loops formed of split concentric tubular conductors joined radially at their axial ends. Adjustment of the separation of these loops provides a change in coupling between the loops effecting a simplified tuning of the resonance of the trap for different expected frequencies of interfering shield current.

U.S. Pat. No. 6,593,744 to Burl et al. issued Jul. 15, 2003 with the title "Multi-channel RF cable trap for magnetic resonance apparatus" and is incorporated herein by reference. In U.S. Pat. No. 6,593,744, Burl et al. describe a multi-channel RF cable trap that blocks stray RF current from flowing on shield conductors of coaxial RF cables of a magnetic resonance apparatus. An inductor is formed by a curved semi-rigid trough constructed of an insulating material coated with an electrically conducting layer. Preferably, the inductor and the cable follow an "S"-shaped path to facilitate good electromagnetic coupling. The RF cables are laid in the trough and the shield conductors inductively couple with the inductor. A capacitor and optional trim capacitor are connected across the trough of the inductor to form a resonant LC circuit tuned to the resonance frequency. The LC circuit inductively couples with the shield conductors to present a signal-attenuating high impedance at the resonance frequency. The resonant circuit is preferably contained in an RF-shielding box with removable lid.

Low-power circuits can use varactors (electrically variable capacitors), field-effect transistors (used as variable gain elements or variable resistors) and like components that are directly electrically-adjustable, for use in adjusting frequency, impedance or other circuit characteristics and parameters, however such components are often unsuitable or inoperative in high fields.

U.S. Pat. No. 6,495,069 issued Dec. 17, 2002 to Lussey et al. with the title "Polymer composition" and is incorporated herein by reference. In U.S. Pat. No. 6,495,069, Lussey et al. describe a polymer composition comprises at least one substantially non-conductive polymer and at least one electrically conductive filler and in the form of granules. Their elastomer material was proposed for devices for controlling or switching electric current, to avoid or limit disadvantages such as the generation of transients and sparks which are associated with the actuation of conventional mechanical switches. They described an electrical conductor composite providing conduction when subjected to mechanical stress or electrostatic charge but electrically insulating when quiescent comprising a granular composition each granule of which comprises at least one substantially non-conductive polymer and at least one electrically conductive filler and is electrically insulating when quiescent but conductive when subjected to mechanical stress. They did not propose a means for electrically activating such switches.

U.S. Pat. No. 8,299,681 to Snyder, Vaughan and Lemaire issued Oct. 30, 2012 with the title "Remotely adjustable reactive and resistive electrical elements and method" and is incorporated herein by reference. In U.S. Pat. No. 8,299,681, Snyder, Vaughan and Lemaire describe an apparatus and method that includes providing a variable-parameter electrical component in a high-field environment and based on an electrical signal, automatically moving a movable portion of the electrical component in relation to another portion of the electrical component to vary at least one of its parameters. In some embodiments, the moving uses a mechanical movement device (e.g., a linear positioner, rotary motor, or pump). In some embodiments of the method, the electrical component has a variable inductance, capacitance, and/or resistance. Some embodiments include using a computer that controls the moving of the movable portion of the electrical component in order to vary an electrical parameter of the electrical component. Some embodiments include using a feedback signal to provide feedback control in order to adjust and/or maintain the electrical parameter. Some embodiments include a non-magnetic positioner connected to an electrical component configured to have its RLC parameters varied by the positioner.

U.S. Pat. No. 8,674,695 to Wiggins issued Mar. 18, 2014 with the title "Radio Frequency Coil Arrangement for High Field Magnetic Resonance Imaging with Optimized Transmit and Receive Efficiency for a Specified Region of Interest, and Related System and Method," and is incorporated herein by reference. In the patent, Wiggins describes exemplary embodiments of a coil arrangement that can include, e.g., a plurality of elements which can be provided at an angle from one another. The angle can be selected to effectuate an imaging of a target region of interest at least one of a predetermined depth or range of depths, for example. In certain exemplary embodiments, according to the Wiggins disclosure, the angle can be selected to effectuate an exemplary predetermined transmit efficiency for at least one of the elements. Additionally, the exemplary angle can be selected to effectuate a predetermined receive sensitivity for at least one of the elements. Further, according to certain exemplary embodiments of a coil arrangement in according to the Wiggins disclosure, the angle can be adjusted manually and/or automatically.

A journal article, "96-Channel Receive-Only Head Coil for 3 Tesla: Design Optimization and Evaluation" by Graham C. Wiggins et al. (Magn. Reson. Med. 2009 September; 62(3): 754-762. doi:10.1002/mrm.22028) describes a receive coil, and is incorporated herein by reference.

U.S. Pat. No. 4,885,539 to Roemer et al. issued Dec. 5, 1989 with the title "Volume NMR coil for optimum signal-to-noise ratio" and is incorporated herein by reference. In U.S. Pat. No. 4,885,539, Roemer et al. describe an RF volume coil with optimized signal-to-noise ratio, for NMR use, has a reduced length $L_c$, which is between about $0.3r_s$ and about $1.5r_s$, where $r_s$ is the radius of a sample-to-be-investigated, contained within the cylindrical volume coil, with the volume coil radius $r_c$ being between about $1.0r_s$ and about $1.6r_s$ the "short" volume coil has an improved SNR for a voxel located substantially on the central plane of the coil, relative to the SNR of a "normal"-length volume coil with $L_c$ greater or equal to $4r_s$.

A journal article, "The NMR Phased Array" by P. B. Roemer et al. (Magn Reson Med. 1990 November; Vol. 16 Issue 262 pages 192-225) describes a phased array receive coil, and is incorporated herein by reference. Roemer et al. describe ways to overlap coil loops (circular loops overlapped by spacing the centers of the circular loops at 0.75 diameter, and square loops by about 0.9 diameter; and the loops are all the same size) to reduce mutual-induction interference.

U.S. Pat. No. 6,534,983 to Boskamp et al. issued Mar. 18, 2003 with the title "Multi-channel phased array coils having minimum mutual inductance for magnetic resonance systems" and is incorporated herein by reference. In U.S. Pat. No. 6,534,983, Boskamp et al. describe a multi-channel phased array coil for use in a magnetic resonance (MR) system is disclosed herein. The phased array coil includes N coils configured in an array, each of the N coils having a geometric shape and overlapping with (N−1) coils to form an overlap area within the array. The geometric shape of each of the coils and the overlap area are configured to cause a mutual inductance between every pair of the coils to be less than 10 percent of the self-inductance of each of the N coils. At least four coils are provided in the phased array coil.

U.S. Pat. No. 6,538,441 issued to Watkins et al. on Mar. 25, 2003 with the title "RF coil for reduced electric field exposure for use in very high field magnetic resonance imaging" and is incorporated herein by reference. In U.S. Pat. No. 6,538,441, Watkins et al. describe an RF coil assembly for a very high field Magnetic Resonance Imaging (MRI) system is provided. The RF coil assembly comprises a plurality of conductors arranged cylindrically and disposed about a patient bore tube of the MRI system. Each of the conductors is configured for the RF coil assembly to resonate at substantially high frequencies. Further, the RF coil assembly comprises a plurality of capacitive elements disposed between and connecting respective ends of the conductors and further disposed in a spaced-apart relationship with the patient bore tube. The capacitive elements are for electrically interconnecting the plurality of conductors at the respective ends of the conductors.

U.S. Pat. No. 6,822,448 issued to Watkins et al. on Nov. 23, 2004 with the title "RF coil for very high field magnetic resonance" and is incorporated herein by reference. In U.S. Pat. No. 6,822,448, Watkins et al. describe an RF coil assembly for a very high field Magnetic Resonance Imaging (MRI) system is provided comprising a plurality of conductors arranged cylindrically and disposed about a cylindrical patient bore tube of the MRI system and a plurality of capacitive elements for electrically interconnecting the plurality of conductors at respective ends of the conductors. The conductors have a width selected for the RF coil assembly to resonate at substantially high frequencies. A very high field Magnetic Resonance Imaging (MRI) system is provided that comprises a RF coil assembly adapted to resonate at substantially high frequencies, a RF coil shield assembly and a plurality of RF drive power cables.

United States Patent Application Publication 2007/0236490 by Casteele et al. published on Oct. 11, 2007 with the title "Medical image display and review system" and is incorporated herein by reference. This publication 2007/0236490 describes an image display and review system for display of medical images represented by a digital image data set wherein a pre-defined number of viewports for display of different image representations is provided and wherein at least some of these viewports are configured to enable sequential display of different image representations deduced from the digital image data set.

United States Patent Application Publication 2013/0106416 by Morich et al. published on May 2, 2013 with the title "ROUTER AND COIL ARRAY FOR ULTRA HIGH FIELD MRI", and is incorporated herein by reference. This publication 2013/0106416 describes a router for use with magnetic resonance systems that selectively routes unique excitation signals generated by a multi-channel radio-frequency (RF) amplifier over transmission lines (Tx) to any one of a plurality of connection panels which each accepts at least one RF coil assembly having multiple coil elements. Each connection panel includes transceiver ports for connecting at least one conductor of the coil elements to a corresponding transceiver channel (T/R). The router selectively routes magnetic resonance signals received by the conductors from the transceiver channels (T/R) to a multi-channel RF receiver. The coin elements may carry sine-mode currents or uniform currents.

U.S. Pat. No. 8,854,042 to Vaughan and Lemaire titled "Method and coils for human whole-body imaging at 7 T," issued Oct. 7, 2014 and claims priority benefit, under 35 U.S.C. § 119(e), of U.S. Provisional Patent Application No. 61/371,170, filed on Aug. 5, 2010 and titled "Coils for human whole-body imaging at 7 T," each of which is incorporated herein by reference in its entirety. A progressive series of five new coils is described. The first coil solves problems of transmit-field inefficiency and inhomogeneity for heart and body imaging, with a close-fitting, 16-channel TEM conformal array design with efficient shield-capacitance decoupling. The second coil progresses directly from the first with automatic tuning and matching, an innovation of huge importance for multi-channel transmit coils. The third coil combines the second, auto-tuned multi-channel transmitter with a 32-channel receiver for best transmit-efficiency, control, receive-sensitivity and parallel-imaging performance. The final two coils extend the innovative technology of the first three coils to multi-nuclear ($^{31}$P-$^{1}$H) designs to make practical human-cardiac imaging and spectroscopy possible for the first time at 7 T.

U.S. Pat. No. 8,217,653 to Vaughan issued Jul. 10, 2012, titled "Multi-channel RF coil system with multi-channel RF coil transceiver detecting more than one frequency at the same time for magnetic resonance imaging systems and methods," and is incorporated herein by reference. This patent describes an RF coil system for magnetic resonance applications that includes a multi-channel RF coil transceiver and a multi-channel RF coil. The RF coil system is structured for reconfiguration among a plurality of operational modes.

U.S. Pat. No. 8,193,809 to Akgun et al. issued Jun. 5, 2012 with the title "Three dimensional RF coil structures for field profiling" and is incorporated herein by reference. This patent describes a radio frequency (RF) that include a plurality of transmission line elements, wherein at least one of the plurality of transmission line elements may have at least one dimension different than a dimension of another one of the plurality of transmission line elements. In some cases, each of the transmission line elements may include a signal line conductor and a ground plane conductor separated by a dielectric.

U.S. Pat. No. 8,380,266 to Vaughan et al. issued Feb. 19, 2013 with the title "Coil element decoupling for MRI" and is incorporated herein by reference. This patent describes an RF coil adjacent an imaging region includes a plurality of conducting coil elements, with each conducting coil element including a proximal portion and a distal portion The RF coil also includes a capacitance between the distal portions of the at least two conducting coil elements. A mutual coupling inductance between at least two conducting coil elements of the plurality of conducting coil elements is substantially cancelled by the capacitance between the distal portions of the at least two conducting coil elements.

U.S. Pat. No. 7,268,554 issued to Vaughan on Sep. 11, 2007, titled "RF coil for imaging system," is incorporated herein by reference. In this patent, an RF coil suitable for use in imaging systems is described, which coil has a dielectric filled cavity formed by a surrounding conducting enclosure, the conducting enclosure preferably being patterned to form continuous electrical paths around the cavity, each of which paths may be tuned to a selected resonant frequency. The patterning breaks up any currents induced in the coil and shortens path lengths to permit higher frequency, and thus higher field strength operation. The invention also includes improved mechanisms for tuning the resonant frequency of the paths, for selectively detuning the paths, for applying signal to the coil, for shortening the length of the coil and for controlling the field profile of the coil and the delivery of field to the object to the image.

U.S. Pat. No. 6,633,161 issued to Vaughan, Jr. on Oct. 14, 2003, titled "RF coil for imaging system," is incorporated herein by reference. In this patent, an RF coil suitable for use in imaging systems is provided which coil has a dielectric filled cavity formed by a surrounding conducting enclosure, the conducting enclosure preferably being patterned to form continuous electrical paths around the cavity, each of which paths may be tuned to a selected resonant frequency. The patterning breaks up any currents induced in the coil and shortens path lengths to permit higher frequency, and thus higher field strength operation. The invention also includes improved mechanisms for tuning the resonant frequency of the paths, for selectively detuning the paths, for applying signal to the coil, for shortening the length of the coil and for controlling the field profile of the coil and the delivery of field to the object to the image.

U.S. Pat. No. 5,557,247 issued to Vaughan, Jr. on Sep. 17, 1996, titled "Radio frequency volume coils for imaging and spectroscopy," is incorporated herein by reference. This patent describes a distributed impedance circuit MR coil design comprised of a transmission line tunable cavity resonator which is well suited for but not limited to use at high frequencies and for large volumes such as in high field (e.g., 4.1 Tesla) clinical MR applications. The distributed circuit transmission line resonator is designed for high frequency, large conductive volume applications where conventional lumped element coil designs fail. A resonant coaxial cavity is variably tuned to the Larmor frequency of interest by tunable transmission line elements. The resonator is effective for large head and body sized volumes, high efficiencies, and broad tuning ranges to frequencies of 500 MHz. The $B_1$ homogeneity of the resonator is a function of the electromagnetic properties of the load itself. Maxwell's equations for the fully time-dependent $B_1$ field predicts "coil" homogeneity with finite-element models of anatomic structure. Coil design and construction, and methods of quadrature driving and double tuning the transmission line resonator, are set forth.

U.S. Pat. No. 5,744,957 issued to Vaughan, Jr. on Apr. 28, 1998, titled "Cavity resonator for NMR systems," is incorporated herein by reference. In this patent, a cavity resonator is disclosed for use in nuclear magnetic resonance (NMR) systems. The resonator has a housing defining a cavity having a selected length and cross-sectional shape. A layer of electrically conductive material is provided around at least a portion of the housing enclosing a dielectric material (air, gasses, TEFLON®, etc.) and the cavity is energized at a Larmor radio frequency useful for NMR systems. The cavity, i.e., a volume enclosed by conductive walls, furthermore, is dimensioned to resonate at the selected radio frequency to thereby generate an alternating magnetic field through the cavity. An opening in the housing is adapted to be placed adjacent an object to be analyzed.

U.S. Pat. No. 5,886,596 issued to Vaughan, Jr. on Mar. 23, 1999, titled "Radio frequency volume coils for imaging and spectroscopy," is incorporated herein by reference. This patent describes an electromagnetic shield for an NMR radio frequency coil designed to resonate at a selected Larmor frequency. The shield includes an electrically conductive layer surrounding the coil. This electrically conductive layer has a thickness substantially the same as one skin depth at the selected Larmor frequency. As such, the conductive layer efficiently conducts radio frequency currents at the selected Larmor frequency thereby conducting and containing the radio frequency coils at the selected Larmor frequency within the coil. Simultaneously, an electrically conductive layer, due to its thinness, very inefficiently conducts eddy currents of the type induced by the lower frequency DC gradient current switching transients the gradients are utilized to magnetically localize an image slice or volume.

Consequently, the conductive layer simultaneously attenuates low frequency eddy current propagation of the type induced by the switching field gradient currents in the NMR application, and therefore does not substantially shield or affect the gradient fields across the coil.

U.S. Pat. No. 7,800,368 issued to Vaughan, et al. on Sep. 21, 2010, titled "High field magnetic resonance," is incorporated herein by reference. In this patent, a magnetic resonance system is disclosed. The system includes a transceiver having a multichannel receiver and a multichannel transmitter, where each channel of the transmitter is configured for independent selection of frequency, phase, time, space, and magnitude, and each channel of the receiver is configured for independent selection of space, time, frequency, phase and gain. The system also includes a magnetic resonance coil having a plurality of current elements, with each element coupled in one to one relation with a channel of the receiver and a channel of the transmitter. The system further includes a processor coupled to the transceiver, such that the processor is configured to execute instructions to control a current in each element and to perform a non-linear algorithm to shim the coil.

U.S. Pat. No. 6,788,056 issued to Vaughan, et al. on Sep. 7, 2004, titled "Radio frequency magnetic field unit with aperature [sic]," and is incorporated herein by reference. In this document, Vaughan et al. describe an apparatus comprises a radio frequency magnetic field unit to generate a desired magnetic field. In one embodiment, the radio frequency magnetic field unit includes a first aperture that is substantially unobstructed and a second aperture contiguous to the first aperture. In an alternative embodiment, the radio frequency magnetic field unit includes a first side aperture, a second side aperture and one or more end apertures. In one embodiment of a method, a current element is removed from a radio frequency magnetic field unit to form a magnetic field unit having an aperture. In an alternative embodiment, two current elements located opposite from one another in a radio frequency magnetic field unit are removed to form a magnetic field unit having a first side aperture and a second side aperture.

U.S. Pat. No. 6,958,607 issued to Vaughan, et al. on Oct. 25, 2005, titled "Assymetric [sic] radio frequency transmission line array," is incorporated herein by reference. In this document, Vaughan et al. describe an apparatus comprises a radio frequency magnetic field unit to generate a desired magnetic field. In one embodiment, the radio frequency magnetic field unit includes a first aperture that is substantially unobstructed and a second aperture contiguous to the first aperture. In an alternative embodiment, the radio frequency magnetic field unit includes a first side aperture, a second side aperture and one or more end apertures. In one embodiment of a method, a current element is removed from a radio frequency magnetic field unit to form a magnetic field unit having an aperture. In an alternative embodiment, two current elements located opposite from one another in a radio frequency magnetic field unit are removed to form a magnetic field unit having a first side aperture and a second side aperture.

U.S. Pat. No. 7,023,209 issued to Zhang, et al. on Apr. 4, 2006 titled "Method and apparatus for magnetic resonance imaging and spectroscopy using microstrip transmission line coils," and is incorporated herein by reference. In this document, Zhang et al. describe an apparatus and method for MRI imaging using a coil constructed of microstrip transmission line (MTL coil) are disclosed. In one method, a target is positioned to be imaged within the field of a main magnetic field of a magnet resonance imaging (MRI) system, a MTL coil is positioned proximate the target, and a MRI image is obtained using the main magnet and the MTL coil. In another embodiment, the MRI coil is used for spectroscopy. MRI imaging and spectroscopy coils are formed using microstrip transmission line. These MTL coils have the advantageous property of good performance while occupying a relatively small space, thus allowing MTL coils to be used inside restricted areas more easily than some other prior art coils. In addition, the MTL coils are relatively simple to construct of inexpensive components and thus relatively inexpensive compared to other designs. Further, the MTL coils of Zhang et al. can be readily formed in a wide variety of coil configurations, and used in a wide variety of ways. Further, while the MTL coils of Zhang et al. work well at high field strengths and frequencies, they also work well at low frequencies and in low field strengths as well.

U.S. Pat. No. 6,969,992 issued to Vaughan, et al. on Nov. 29, 2005, titled "Parallel transceiver for nuclear magnetic resonance system," is incorporated herein by reference. This patent describes an excitation and detection circuit having individually controllable elements for use with a multi-element radio frequency coil. Characteristics of the driving signal, including, for example, the phase, amplitude, frequency and timing, from each element of the circuit is separately controllable using small signals. Negative feedback for the driving signal associated with each coil element is derived from a receiver coupled to that coil element.

U.S. Pat. No. 7,710,117 issued to Vaughan, et al. on May 4, 2010, titled "Multi-current elements for magnetic resonance radio frequency coils," is incorporated herein by reference. This patent describes a current unit having two or more current paths that allow control of magnitude, phase, time, frequency and position of each of element in a radio frequency coil. For each current element, the current can be adjusted as to a phase angle, frequency and magnitude. Multiple current paths of a current unit can be used for targeting multiple spatial domains or strategic combinations of the fields generated/detected by combination of elements for targeting a single domain in magnitude, phase, time, space and frequency.

U.S. Pat. No. 7,514,926 issued to Adriany, et al. on Apr. 7, 2009, titled "Spatially reconfigurable magnetic resonance coil," is incorporated herein by reference. This patent discusses, among other things, a system and method for a coil having a plurality of resonant elements and an adjustable frame. A position of at least one resonant element can be adjusted relative to at least one other resonant element. A variable impedance is coupled to adjacent resonant elements and the impedance varies as a function of a separation distance. Cables are coupled to each resonant element and are gathered at a junction in a particular manner.

U.S. Pat. No. 7,598,739 issued to Vaughan, Jr., et al. on Oct. 6, 2009, titled "Radio frequency gradient, shim and parallel imaging coil," is incorporated herein by reference. This patent describes a plurality of linear current elements that are configured about a specimen to be imaged. A current in each current element is controlled independent of a current in other current elements to select a gradient and to provide radio frequency shimming. Each current element is driven by a separate channel of a transmitter and connected to a separate channel of a multi-channel receiver. The impedance, and therefore, the current, in each current element is controlled mechanically or electrically.

U.S. Pat. No. 7,633,293 issued to Olson, et al. on Dec. 15, 2009, titled "Radio frequency field localization for magnetic resonance," is incorporated herein by reference. This patent describes that technology for controlling non-uniformity in the $B_1$ field includes selecting the phase, magnitude, frequency, time, or spatial relationship among various elements of a multi-channel excitation coil in order to control the radio frequency (RF) power emanating from the coil antenna elements. Non-uniformity can be used to steer a constructively interfering $B_1$ field node to spatially correlate with an anatomic region of interest. A convex (quadratically constrained quadratic problem) formulation of the $B_1$ localization problem can be used to select parameters for exciting the coil. Localization can be used in simulated Finite Difference Time Domain $B_1$ field human head distributions and human head phantom measurement.

United States Patent Publication 2015/0323624 by Feinberg and Schillak, published Nov. 12, 2015 and titled "Device and method for loops-over-loops MRI coils," is incorporated by reference. Publication 2015/0323624 describes a method and apparatus for receiving (RX) radio-frequency (RF) signals suitable for MRI and/or MRS from MRI "coil loops" (antennae) that are overlapped and/or concentric, and each of which has a preamplifier and frequency-tuning circuitry and an impedance-matching circuitry, but wherein the loops optionally sized differently and/or located at different elevations (distances from the patient's tissue) in order to extract signal from otherwise cross-coupled coil loops and to improve signal-to-noise ratio (SNR) in images made from the received signal.

United States Patent Publication 2015/0196226 by Tramm et al., published Jul. 16, 2015 and titled "Method and positionable patient-interface apparatus for an MRI system," which claims priority to U.S. Provisional Patent Application No. 61/906,409 filed Nov. 19, 2013 titled "Method and apparatus for adjustable earpieces in an MRI system," are each incorporated herein by reference in their entirety. Publication 2015/0196226 describes an apparatus and method for imaging a patient in an MRI system. This includes a frame, and at least one assembly that includes a patient-interface positioner connected to a reference position on the frame, a first lockable joint on the positioner; and a patient interface connected to a patient-proximal end of the positioner by a second joint, wherein the first patient-interface is moveably positioned to a selected pitch angle, a selected yaw angle, and a selected one of a plurality of distances relative to the reference position on the frame. The first lockable joint is configured to be tightened to yieldably hold the first patient-interface at the selected pitch and yaw angles, and at the selected one of the plurality of distances, relative to the reference position. Optionally a second substantially similar patient-interface and assembly are provided. The earpiece(s) optionally include audio transducer(s) and/or RF coil(s).

U.S. Pat. No. 9,160,295 to Waks et al. issued Oct. 13, 2015 with the title "Snap-on coaxial cable balun and method for trapping RF current on outside shield of coax after installation" and is incorporated herein by reference. Waks et al. describe an apparatus and method for a radially attachable RF trap attached from a side to a shielded RF cable. In some embodiments, the RF trap creates a high impedance on the outer shield of the RF cable at a frequency of RF signals carried on at least one inner conductor of the cable. In some embodiments, an RF-trap apparatus for blocking stray signals on a shielded RF cable that has a peripheral shield conductor and an inner conductor for carrying RF signals includes: a case; an LC circuit having a resonance frequency equal to RF signals carried on the inner conductor; projections that pierce and connect the LC circuit to the shield conductor; and an attachment device that holds the case to the cable with the LC circuit electrically connected to the shield conductor of the shielded RF cable.

There remains a long-felt need for a configurable close-fitting MRI head coil with improved SNR from received signals in an MRI system.

SUMMARY OF THE INVENTION

In some embodiments, a plurality of head-coil parts is provided, each having a subset of the total number of coil loops. In some embodiments, each one of a movable plurality of the plurality of head-coil parts is connected to a coil-part positioner that adjusts the position of the movable head-coil part from an open position that provides easy access and positioning of the patient's head, to a more closed conforming position that is snug against the patient's head (with a small distance between the coil loops and the patient's tissue), and that provides improved signal-to-noise and better images than conventional head coils that are not adjustable as to the distance between the coil loops or elements and the patient's head. In some embodiments, each coil-part positioner is manually adjusted by an MRI health-care professional to position the respective head-coil part to be at the desired position. In some embodiments, one or more of the manually adjustable head-coil parts are connected to slidable holders (e.g., dove-tail-like sliding bracket 143 on guide track 144 of FIG. 1) and/or clamping hinged holders (e.g., arm 152, which connects coil portion 151 to rotating clamping mechanism 153, which can be positioned at various angles in sleeve 154 of FIG. 1). In some embodiments, one or more of the manually adjustable head-coil parts are connected to bendable modular positioners (in some embodiments, e.g., connected to the base unit) such as ½-inch or ¾-inch (about 12.7-mm-diameter or about 19-mm-diameter) LOC-LINE® modular hoses available from Lockwood Products (www.loc-line.com).

In some embodiments, each coil-part positioner includes a motorized actuator that can be remotely adjusted by an MRI health-care professional to reposition the respective head-coil part to be at a more comfortable position for the patient (e.g., to temporarily move the head-coil part slightly away from the patient to give the patient a rest break), or a more effective position for obtaining a particular image. In some embodiments, the remote-control actuator coil-part positioner(s) adjusts the positions of respective ones of the head-coil parts after the patient is in the MRI magnet, for example, in the middle of an MRI imaging session, in order to give the patient a break during a lengthy MRI examination. In some embodiments, the remote-control actuator coil-part positioners further include pressure sensors in one or more locations on the patient-facing side of the head-coil parts, and signals from the pressure sensors are used by the MRI health-care professional (or automatically by a computerized controller) to provide enough pressure to immobilize the patient's head without putting too much pressure that would injure the patient or make the patient unduly uncomfortable. In some embodiments, a first base part, optionally having no coils, is used to provide support of the plurality of coil parts, wherein the plurality of coil parts includes a second part holding back-of-the-head coil loops, a third part holding right-side-of-the-head coil loops, a fourth part holding right-side-of-the-head coil loops, and a fifth part holding top-of-the-head coil loops. In some embodiments, each of the second, third, fourth and fifth parts is position-adjustable and thus can be moved to and clamped to be snug against the patient's head or otherwise affixed to a plurality of different given locations on the first base part.

In some embodiments, a plurality of fiducial marks are provided such that a user (e.g., the MRI-machine operator) can note the exact positions and relative locations to which the various parts have been placed for a patient examination, and then during later examinations, the user can again place each of the parts in the same physical relationship to the other parts so meaningful examination-to examination comparisons can be made. (Otherwise, the differences between the results of the various examination could be due to different placements of the coil parts rather than to differences in the patient's condition.) Some embodiments of the invention include a kit of parts that can be substituted for one another, such that some of the parts may contain fewer or no coil loops, in order that more loops concentrated in other parts are utilized to pick up more detailed signals from other parts of the head, especially when the MRI console has a limited number of channels to receive different signals from different coil loops. In some embodiments, the kit of parts includes substitute parts that conform to different head sizes and shapes, wherein the user is enabled to pick-and-choose combinations of parts that better fit the head of a particular patient. In some embodiments, the second part holding the back-of-the-head coil loops has tapered edges to allow overlap of its coil loops with the adjacent coil loops in the third part holding the right-side-of-the-head coil loops, and the fourth part holding the right-side-of-the-head coil loops.

In some embodiments, the present invention provides overlapped and/or concentric radio-frequency (RF) MRI coils that are optionally located at different elevations (distances from the patient's tissue) in order to extract signal from cross-coupled coil loops and to improve signal-to-noise ratio (SNR) of the received signal. A large number of independent receive pre-amplifiers (preamps) are used to collect the received signal and the MR image reconstructed from the received signal. In some embodiments, a plurality of preamps is connected to each of a plurality of coil loops. In some embodiments, the received signals are decoded (e.g., using differential analog amplifiers on the analog signals, or are digitally processed to remove common mode signal, and to improve SNR).

In contrast to U.S. Pat. No. 6,534,983 to Boskamp et al. (where the geometric shape of each of the coil loops and the overlap area are configured to cause a mutual inductance between every pair of the coil loops to be less than 10 percent of the self-inductance of each of the N coils), some embodiments of the present invention use concentric and/or overlapped coil loops, each coil loop having one or more individual preamplifiers. In some embodiments, the plurality of loops of the present invention will be arranged to reduce mutual inductance, but the greater number of coil loops is used to advantage in order to achieve greater signal-to-noise ratio (SNR) in spite of the greater mutual inductance due to overlapping and/or concentric coil loops. The outputs of the plurality of preamplifiers are analyzed and decoded relative to one another to electronically and/or computationally remove signal due to the mutual inductance between various pairs of the coil loops.

In some embodiments, a set of coil loops have each of their outputs phase shifted by possibly different amounts, and have their respective amplitudes varied by possibly different amounts, and their signals added or subtracted from one another by decoder circuitry to improve the SNR.

Each one of the patents, published patent applications, and journal articles mentioned in this specification is incorporated herein by reference. In some embodiments, the pieces and parts that are described in the patents, published patent applications, and journal articles incorporated herein by reference are added to, combined with or substituted for individual parts as described herein, and it is intended that the resulting combination is a combination within the present invention.

DESCRIPTION OF PREFERRED EMBODIMENTS

Figure 1:
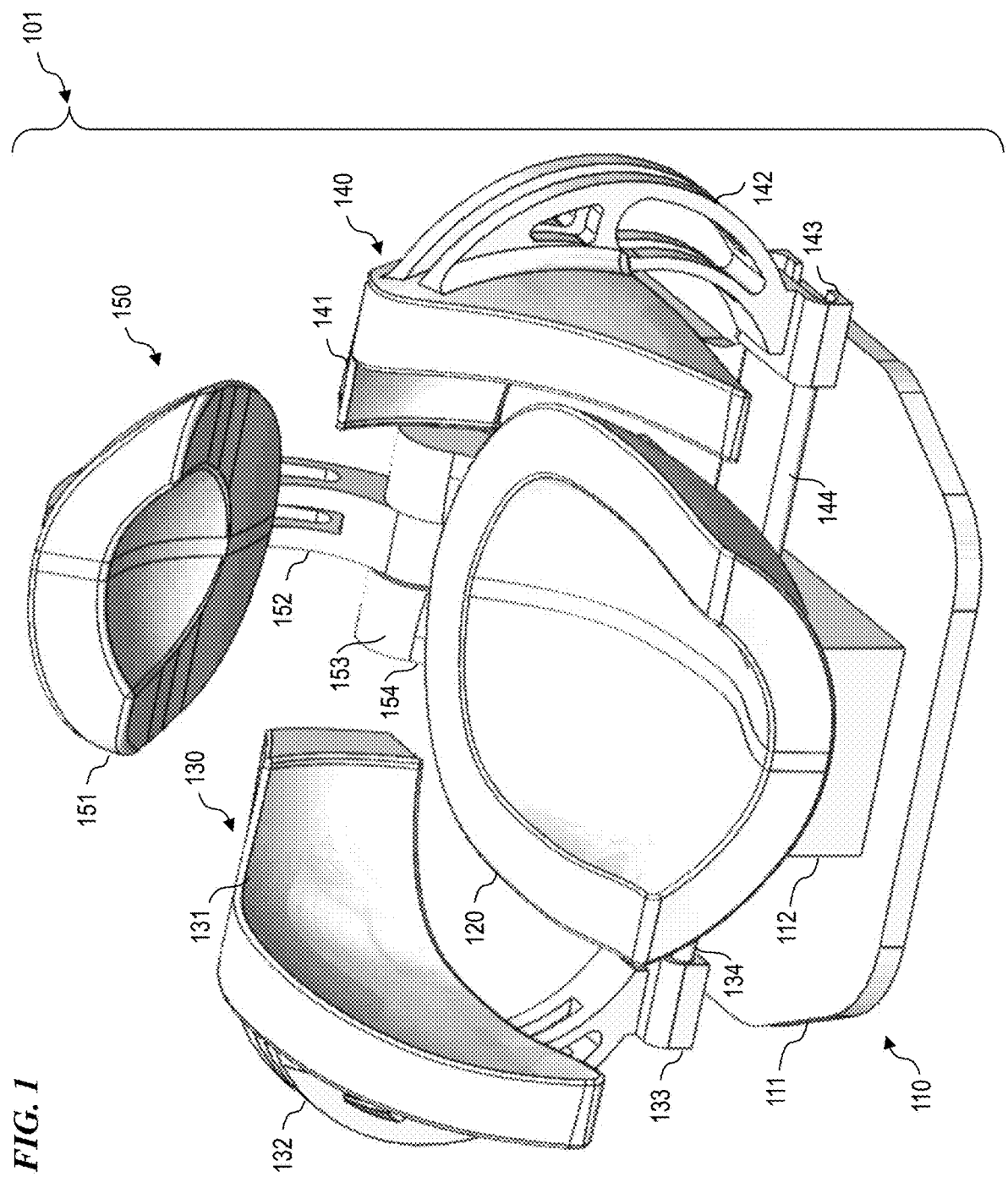
FIG. 1 is a perspective-view diagram of a head coil system 101 in an open position, according to some embodiments of the present invention.

Although the following detailed description contains many specifics for the purpose of illustration, a person of ordinary skill in the art will appreciate that many variations and alterations to the following details are within the scope of the invention. Specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

It is specifically contemplated that the present invention includes embodiments having combinations and subcombinations of the various embodiments and features that are individually described herein (i.e., rather than listing every combinatorial of the elements, this specification includes descriptions of representative embodiments and contemplates embodiments that include some of the features from one embodiment combined with some of the features of another embodiment, including embodiments that include some of the features from one embodiment combined with some of the features of embodiments described in the patents and application publications incorporated by reference in the present application). Further, some embodiments include fewer than all the components described as part of any one of the embodiments described herein.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

As used herein, a non-magnetic mechanical movement device is any electrically-controlled device (such as a linear positioner, rotary motor, or pump) made of materials that do not move (or move to a substantially negligible amount) due to a high magnetic field when subjected to the high magnetic field. Such devices can be placed within the high magnetic field of a magnetic-resonance machine or the superconducting magnet of a particle accelerator without the danger of the device moving due to the magnetic field and/or without the undesirable result of changing the magnetic field due to their presence. In many of the descriptions herein, the term "motor" (such as motor 140) will be used as an example of such a non-magnetic mechanical movement device, however one of skill in the art will recognize that in other embodiments, the "motor" can be implemented as a linear or rotary motor device using suitable linkages, or as a pump that uses a liquid or pneumatic fluid to effectuate the described movement.

FIG. 1 is a perspective-view diagram of a head coil system 101 in an open position, according to some embodiments of the present invention. In some embodiments, head coil system 101 includes a base part 110, a back-of-head coil part 120, a right-side-of-head coil part 130, a left-side-of-head coil part 140, and a top-of-head coil part 150. In some embodiments, each of these parts 110, 120, 130, 140, and 150 can be separated from the rest, and each can be reconnected to the others in a plurality of adjustable angles and/or distances relative to one another to conform to different sizes and shapes of patient's heads and the relative orientation of the patient's head to the rest of the patient's body as the patient lies on an MRI table for an MRI scan within the bore of an MRI magnet. In some embodiments, a clamping mechanism 126 (see FIG. 13) is provided for back-of-head coil part 120 to hold and adjust for the position of the patient's head relative to the rest of the patient's body, and annotated fiducial marks 125 (see FIG. 13) are provided to allow recording of the position of back-of-head coil part 120 so that its position can be repeated for future examinations. Similarly, in some embodiments, a clamping mechanism 136 is provided for each of right-side-of-head coil part 130, left-side-of-head coil part 140, and clamping mechanism 153 for top-of-head coil part 150 to hold and adjust their positions, and respective annotated fiducial marks 135 (see FIG. 10), annotated fiducial marks 145 (see FIG. 13 and FIG. 14) and annotated fiducial marks 155 (see FIG. 13 and FIG. 14) are provided to allow recording of the position of the respective head coil parts 130, 140 and 150 so that their positions can be repeated for future examinations of each different patient. In some embodiments, right-side-of-head coil part 130 includes a coil portion 131 holding a plurality of coil loops or elements (e.g., such as shown and described in U.S. Patent Application Publication 2015/0323624 by Feinberg et al., titled "Device and method for loops-over-loops MRI coils," which is incorporated by reference). In some embodiments, arm 132 connects coil portion 131 to sliding bracket 133, which can be slid along track 134 and clamped into a suitable position (fiducial marks 135 allow repeatable positioning to the same customized position for each exam of a given patient). In some embodiments, left-side-of-head coil part 140 is a mirror image of part 130, and it includes a coil portion 141, and arm 142 connects coil portion 141 to sliding bracket 143, which can be slid along track 144 and clamped into a suitable position (fiducial marks 145 allow repeatable positioning to the same customized position for each exam of a given patient). In some embodiments, top-of-head coil part 150 includes a coil portion 151, and arm 152 connects coil portion 151 to rotating clamping mechanism 153, which can be positioned at various angles in sleeve 154 and clamped into a suitable angle (fiducial marks 155 allow repeatable positioning to the same customized angle for each exam of a given patient). In some embodiments, each of the coil parts 120, 130, and 140 also include an angle adjustment for more flexibility in positioning and orientation. In some embodiments, coil part 150 also includes a sliding bracket and clamp (not shown here, but similar to, for example, track 133 and sliding bracket 134) to allow it to be positioned further out or closer in for any given angle position. In some embodiments, base part 110 includes a base plate 111, a riser 112 used to position and hold back-of-head coil part 120 in its desired location and/or orientation.

In other embodiments, electrical and/or optical position and/or angle sensors are used to supplement and/or replace the annotated fiducial marks 125, 135, 145 and 155. In some embodiments, mechanical actuators are provided along with the position/angle sensors to position the various parts 120, 130, 140 and 150 to their desired positions and orientations relative to one another and relative to base 110, in order to automatically obtain the same experimental positions for each of a plurality of exams performed at different times for a given patient.

For the remaining Figures showing head coil system 101, the like reference numbers refer to the corresponding parts described for FIG. 1.

Figure 2:
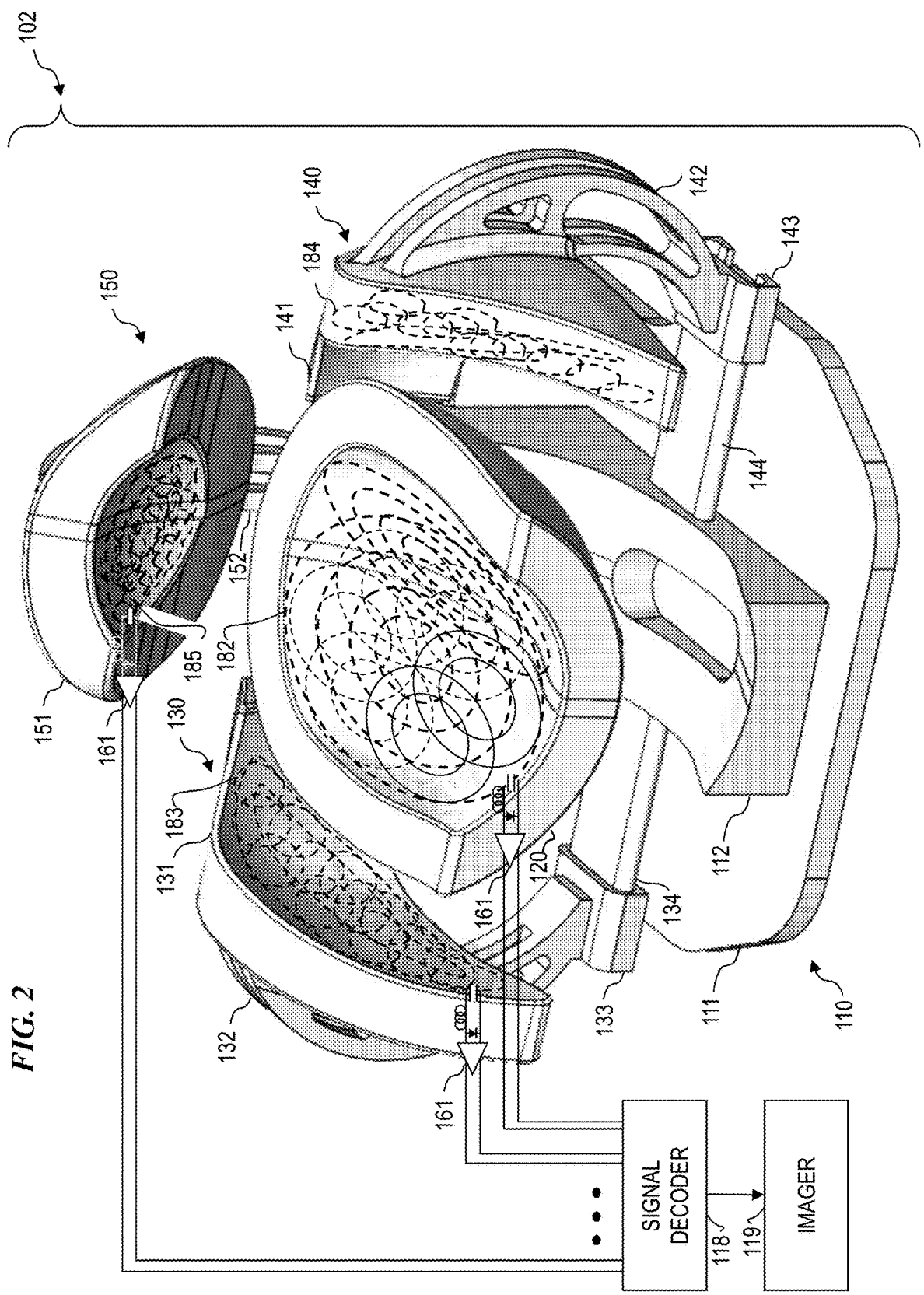
FIG. 2 is a perspective-view diagram of a head coil system 102 in an open position, showing schematic diagrams of some coils loops and tune-and-match on-coil preamps, according to some embodiments of the present invention.

FIG. 2 is a perspective-view diagram of a head coil system 102 in an open position, showing schematic diagrams of some coils loops and tune-and-match on-coil preamps, according to some embodiments of the present invention. FIG. 2 also shows a schematic representation of RF-receiving loops 182 in back-of-head coil part 120. In some embodiments, loops 182 in back-of-head coil part 120 are coupled via a plurality of tune-and-match preamplifier circuits 194 (see also FIG. 21) to signal decoder 118, which extracts combination information from a plurality of simultaneously received signals and passes the extracted combination information to imager unit 119, which forms and outputs image data for display on a monitor and/or for storage and later analysis. In some embodiments, loops 185 in top-of-head coil part 150 are also coupled via a plurality of auto-tune-and-match preamplifier circuits 194 (see also FIG. 21) to signal decoder 118. Similarly, corresponding loops 183 in right-side-of-head coil part 130 (and corresponding loops 184 shown in left-side-of-head coil part 140) are each connected via other pluralities of tune-and-match preamplifier circuits 194 (see also FIG. 21) to signal decoder 118. In some embodiments, suitable shielded cables with adjustable baluns (such as are described in U.S. Pat. No. 9,160,295 to Waks et al. issued Oct. 13, 2015 with the title "Snap-on coaxial cable BALUN and method for trapping RF current on outside shield of coax after installation," which is incorporated herein by reference) are used to couple each of the auto-tune-and-match preamplifier circuits 194 to signal decoder 118.

Figure 3:
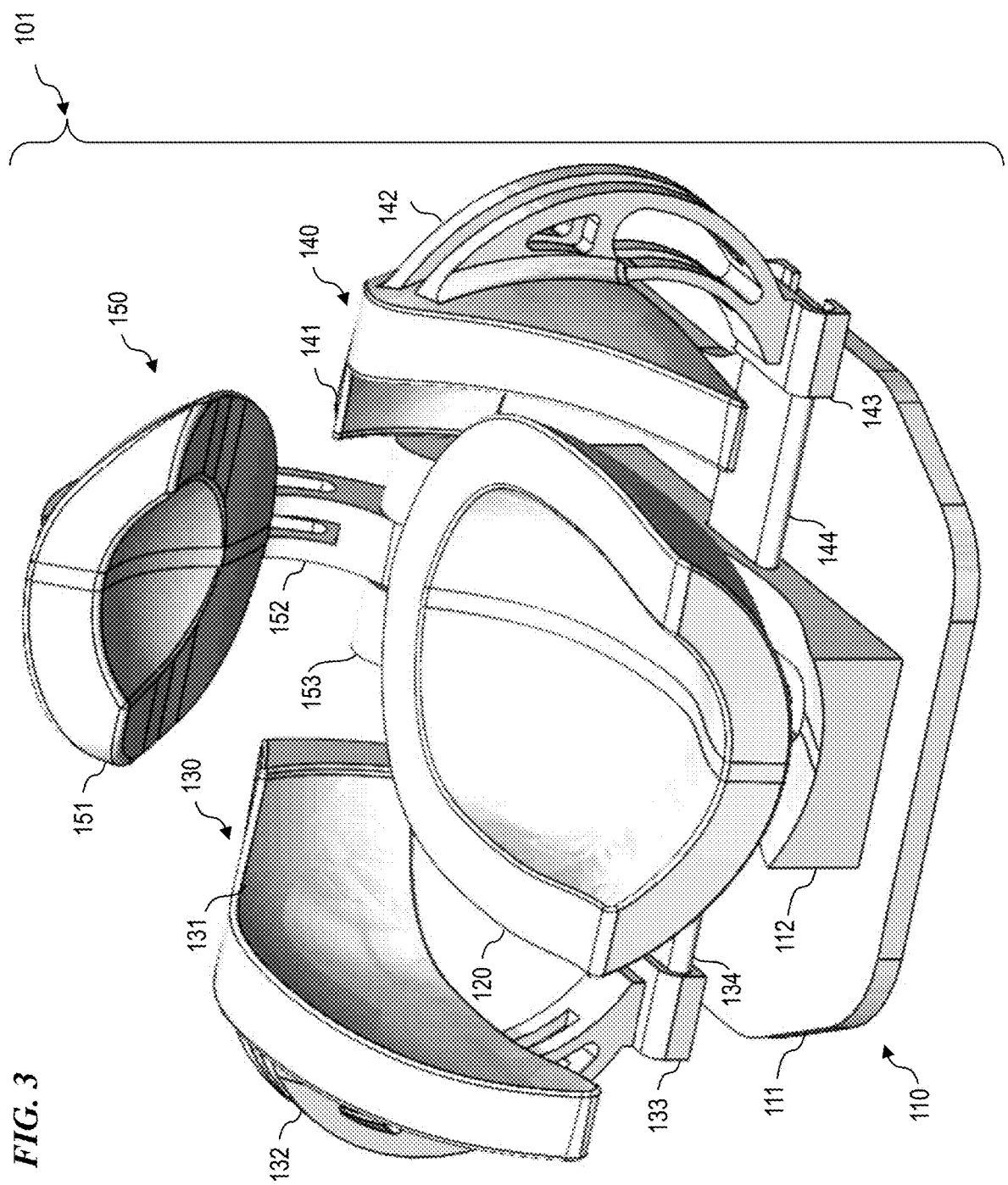
FIG. 3 is a perspective-view diagram of a head coil system 101 in an open position with the back-of-head coil part 120 partially lowered into position, according to some embodiments of the present invention.

FIG. 3 is a perspective-view diagram of a head coil system 101 in an open position with the back-of-head coil part 120 partially lowered into position, according to some embodiments of the present invention.

Figure 4:
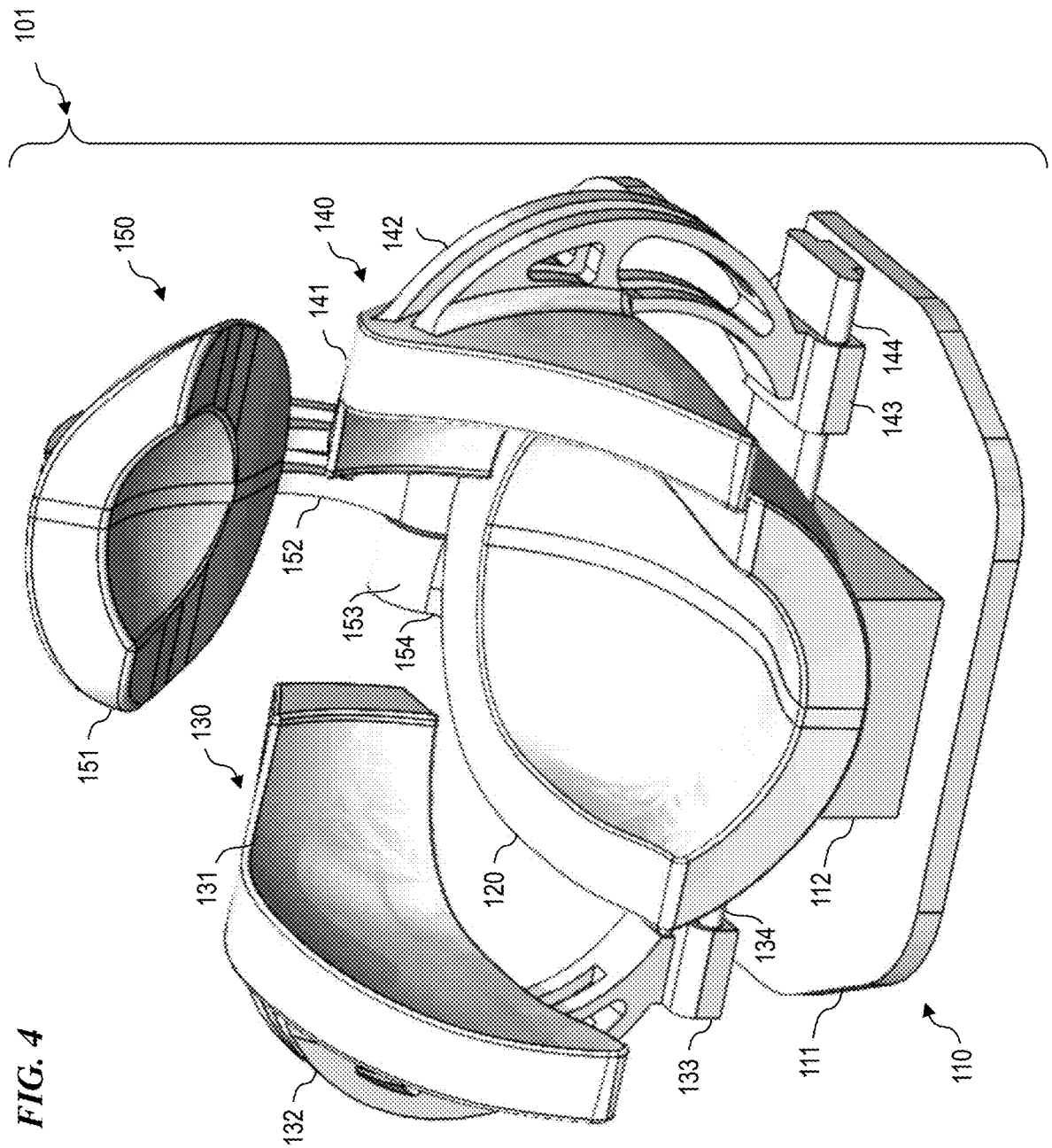
FIG. 4 is a perspective-view diagram of a head coil system 101 in an open position with the back-of-head coil part 120 lowered into position and left-side-of-head coil part 140 partially moved into position, according to some embodiments of the present invention.

FIG. 4 is a perspective-view diagram of a head coil system 101 in an open position with the back-of-head coil part 120 lowered into position and left-side-of-head coil part 140 partially moved into position, according to some embodiments of the present invention.

Figure 5:
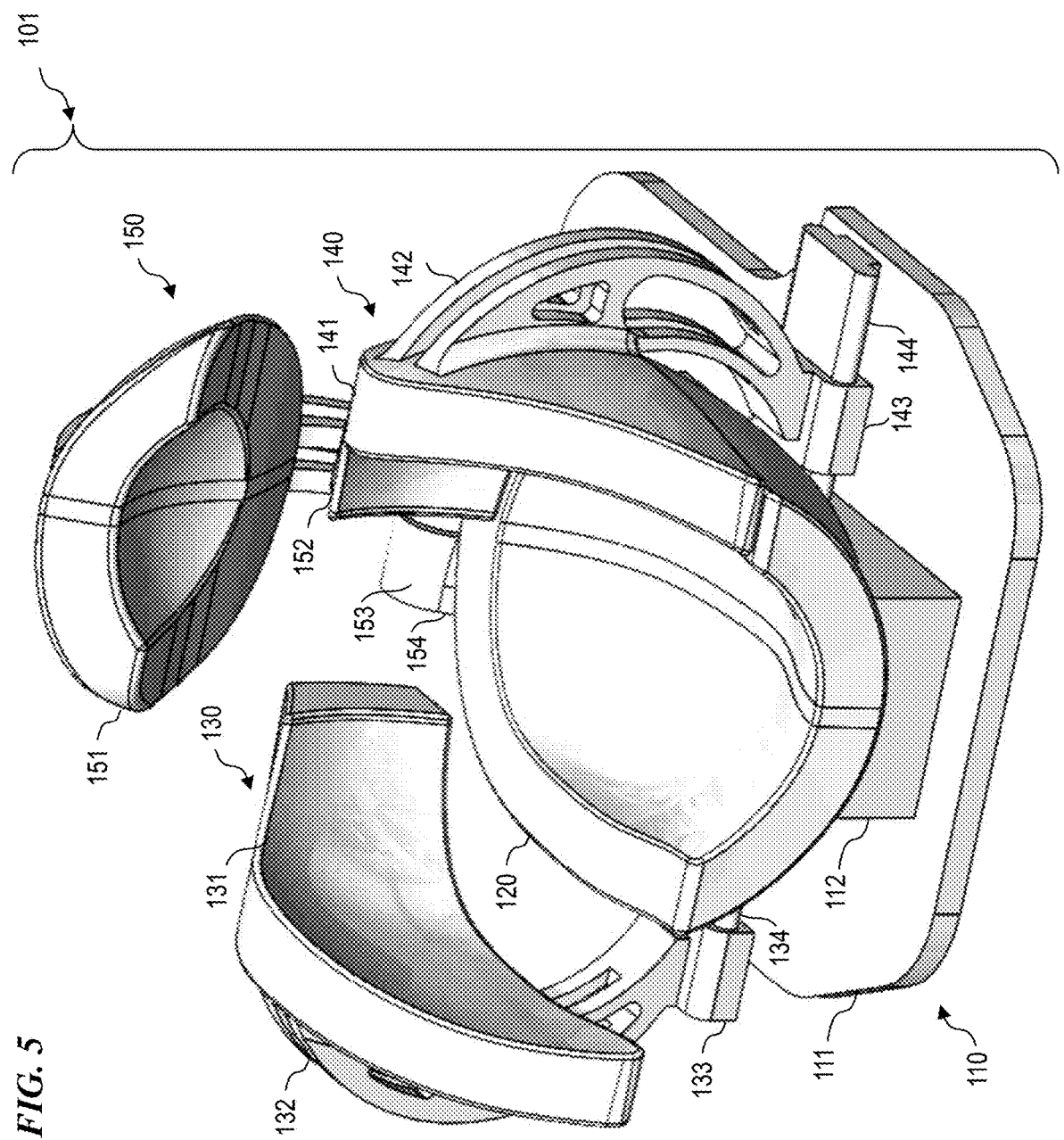
FIG. 5 is a perspective-view diagram of a head coil system 101 in an open position with the back-of-head coil part 120 lowered into position and left-side-of-head coil part 140 moved into position, according to some embodiments of the present invention.

FIG. 5 is a perspective-view diagram of a head coil system 101 in an open position with the back-of-head coil part 120 lowered into position and left-side-of-head coil part 140 moved into position, according to some embodiments of the present invention.

Figure 6:
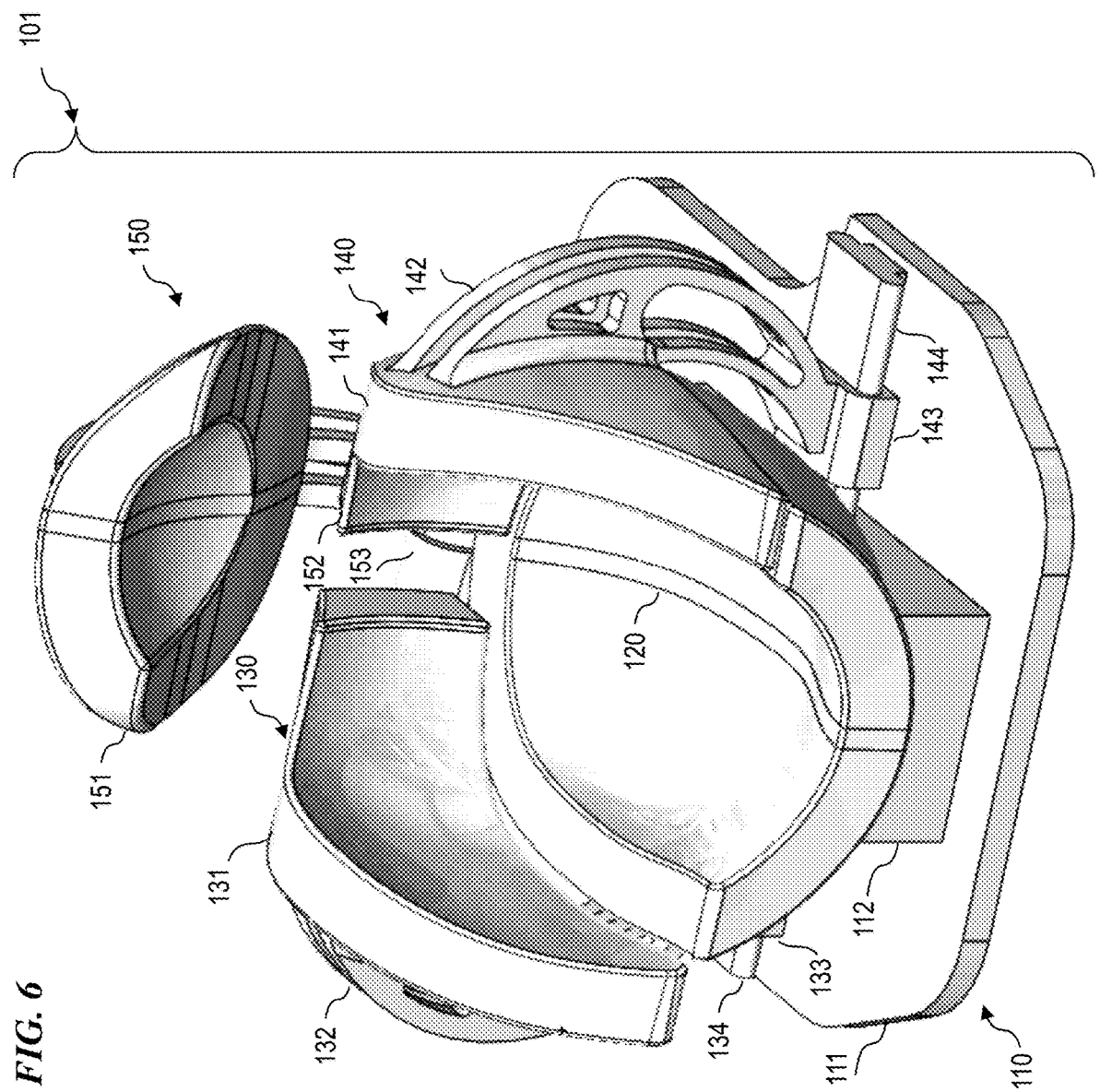
FIG. 6 is a perspective-view diagram of a head coil system 101 in an open position with the back-of-head coil part 120 lowered into position, left-side-of-head coil part 140 moved into position and right-side-of-head coil part 130 partially moved into position, according to some embodiments of the present invention.

FIG. 6 is a perspective-view diagram of a head coil system 101 in an open position with the back-of-head coil part 120 lowered into position, left-side-of-head coil part 140 moved into position and right-side-of-head coil part 130 partially moved into position, according to some embodiments of the present invention.

Figure 7:
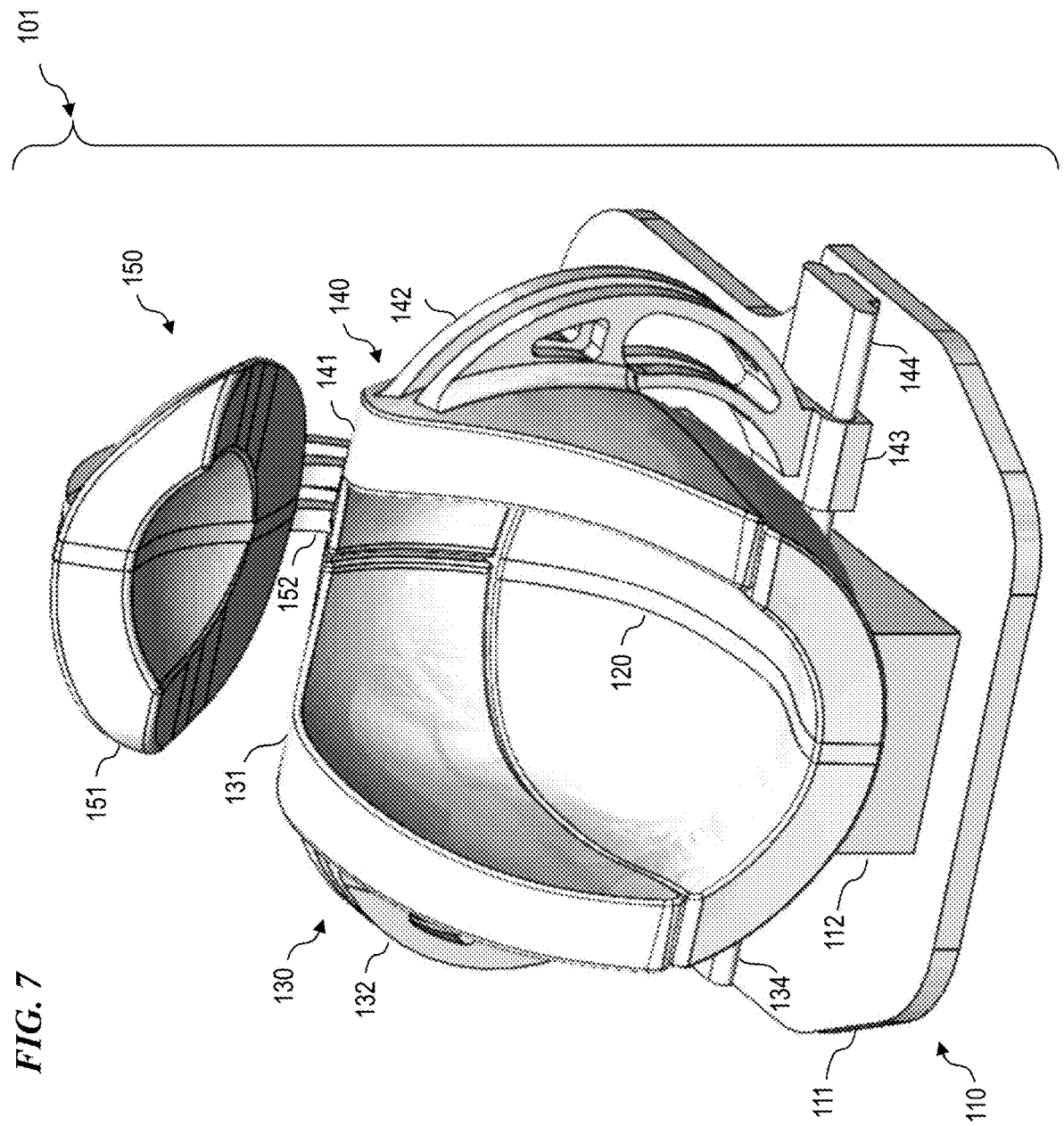
FIG. 7 is a perspective-view diagram of a head coil system 101 in an open position with the back-of-head coil part 120 lowered into position, left-side-of-head coil part 140 moved into position and right-side-of-head coil part 130 moved into position, according to some embodiments of the present invention.

FIG. 7 is a perspective-view diagram of a head coil system 101 in an open position with the back-of-head coil part 120 lowered into position, left-side-of-head coil part 140 moved into position and right-side-of-head coil part 130 moved into position, according to some embodiments of the present invention.

Figure 8:
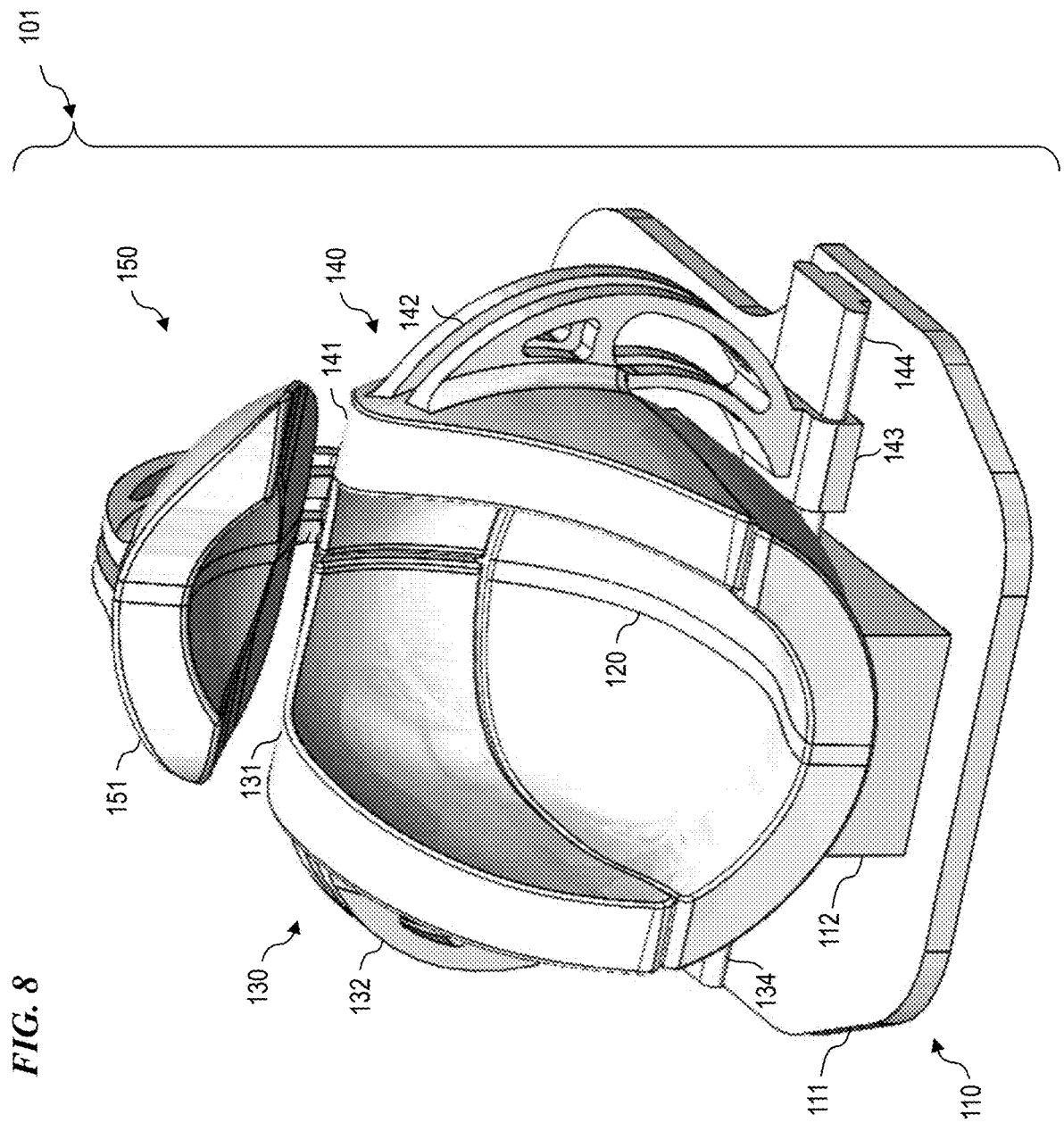
FIG. 8 is a perspective-view diagram of a head coil system 101 in an open position with the back-of-head coil part 120 lowered into position, left-side-of-head coil part 140 moved into position, right-side-of-head coil part 130 moved into position and top-of-head coil part 150 partially moved into position, according to some embodiments of the present invention.

FIG. 8 is a perspective-view diagram of a head coil system 101 in an open position with the back-of-head coil part 120 lowered into position, left-side-of-head coil part 140 moved into position, right-side-of-head coil part 130 moved into position and top-of-head coil part 150 partially moved into position, according to some embodiments of the present invention.

Figure 9:
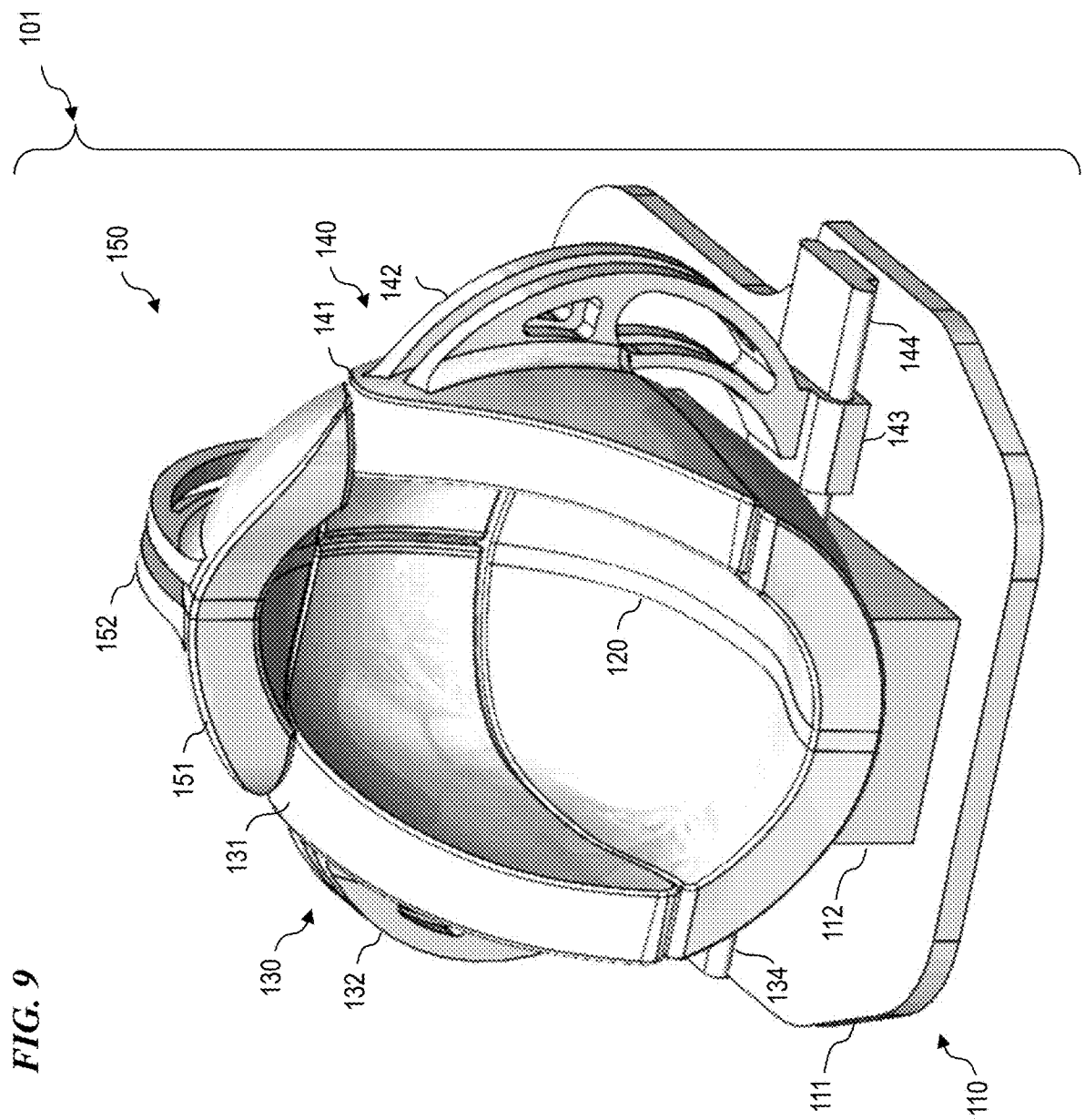
FIG. 9 is a perspective-view diagram of a head coil system 101 in an open position with the back-of-head coil part 120 lowered into position, left-side-of-head coil part 140 moved into position, right-side-of-head coil part 130 moved into position and top-of-head coil part 150 moved into position, according to some embodiments of the present invention.

FIG. 9 is a perspective-view diagram of a head coil system 101 in an open position with the back-of-head coil part 120 lowered into position, left-side-of-head coil part 140 moved into position, right-side-of-head coil part 130 moved into position and top-of-head coil part 150 moved into position, according to some embodiments of the present invention.

Figure 10:
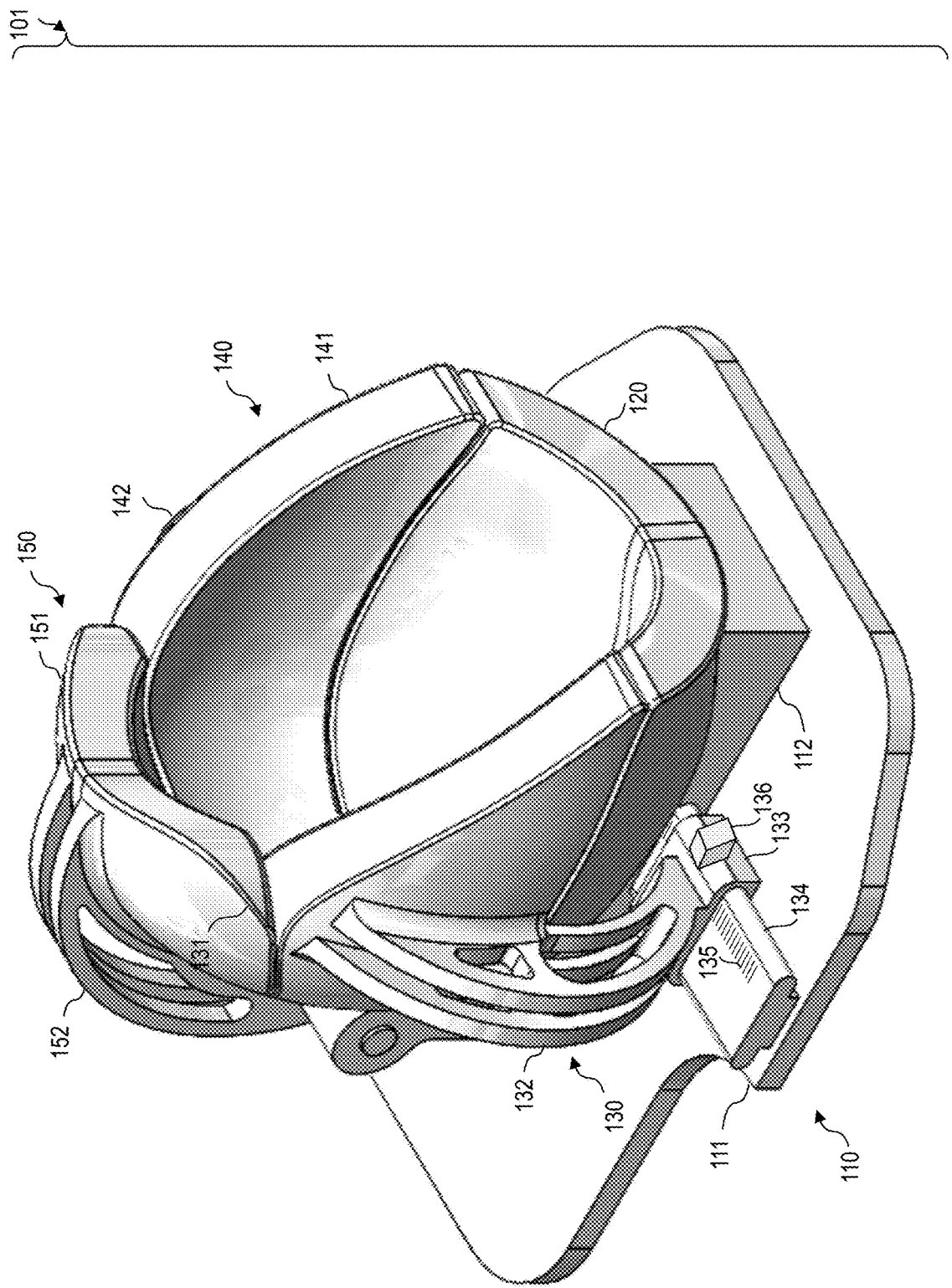
FIG. 10 is another perspective-view diagram, from a different angle than that of FIG. 9, of a head coil system 101 in an open position with the back-of-head coil part 120 lowered into position, left-side-of-head coil part 140 moved into position, right-side-of-head coil part 130 moved into position and top-of-head coil part 150 moved into position, according to some embodiments of the present invention.

FIG. 10 is another perspective-view diagram, from a different angle than that of FIG. 9, of a head coil system 101 in an open position with the back-of-head coil part 120 lowered into position, left-side-of-head coil part 140 moved into position, right-side-of-head coil part 130 moved into position and top-of-head coil part 150 moved into position, according to some embodiments of the present invention.

Figure 11:
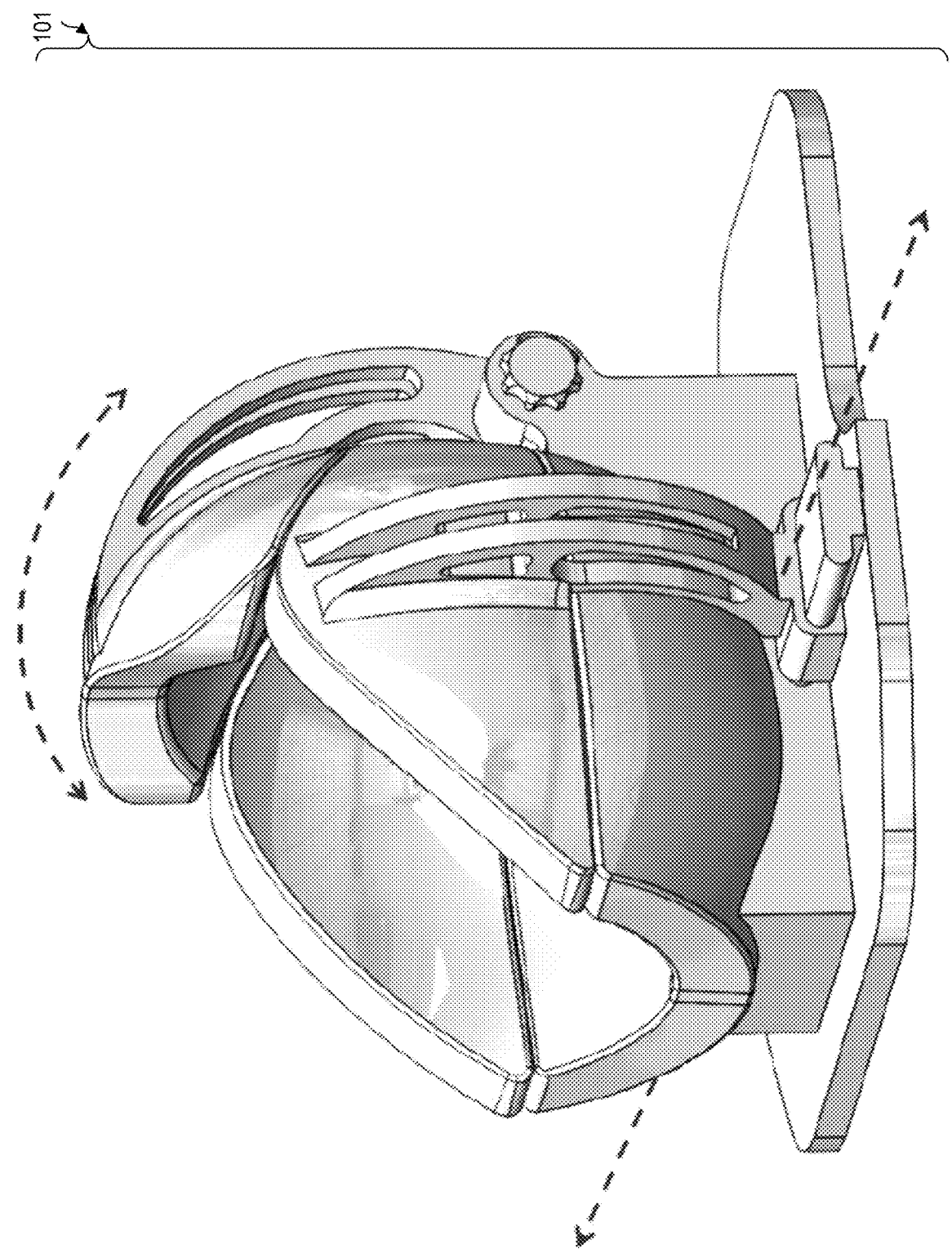
FIG. 11 is another perspective-view diagram, from yet a different angle than that of FIG. 9, of a head coil system 101 in an open position with the back-of-head coil part 120 lowered into position, left-side-of-head coil part 140 moved into position, right-side-of-head coil part 130 moved into position and top-of-head coil part 150 moved into position, according to some embodiments of the present invention.

FIG. 11 is another perspective-view diagram, from yet a different angle than that of FIG. 9, of a head coil system 101 in an open position with the back-of-head coil part 120 lowered into position, left-side-of-head coil part 140 moved into position, right-side-of-head coil part 130 moved into position and top-of-head coil part 150 moved into position, according to some embodiments of the present invention. As shown in FIG. 11, top-of-head coil part 150 can be moved angularly in an arc 157 around the axis of clamping/locking knob 153. In some embodiments, left-side-of-head coil part 140 slid along path 147 and right-side-of-head coil part 130 can be slid along path 137.

Figure 12:
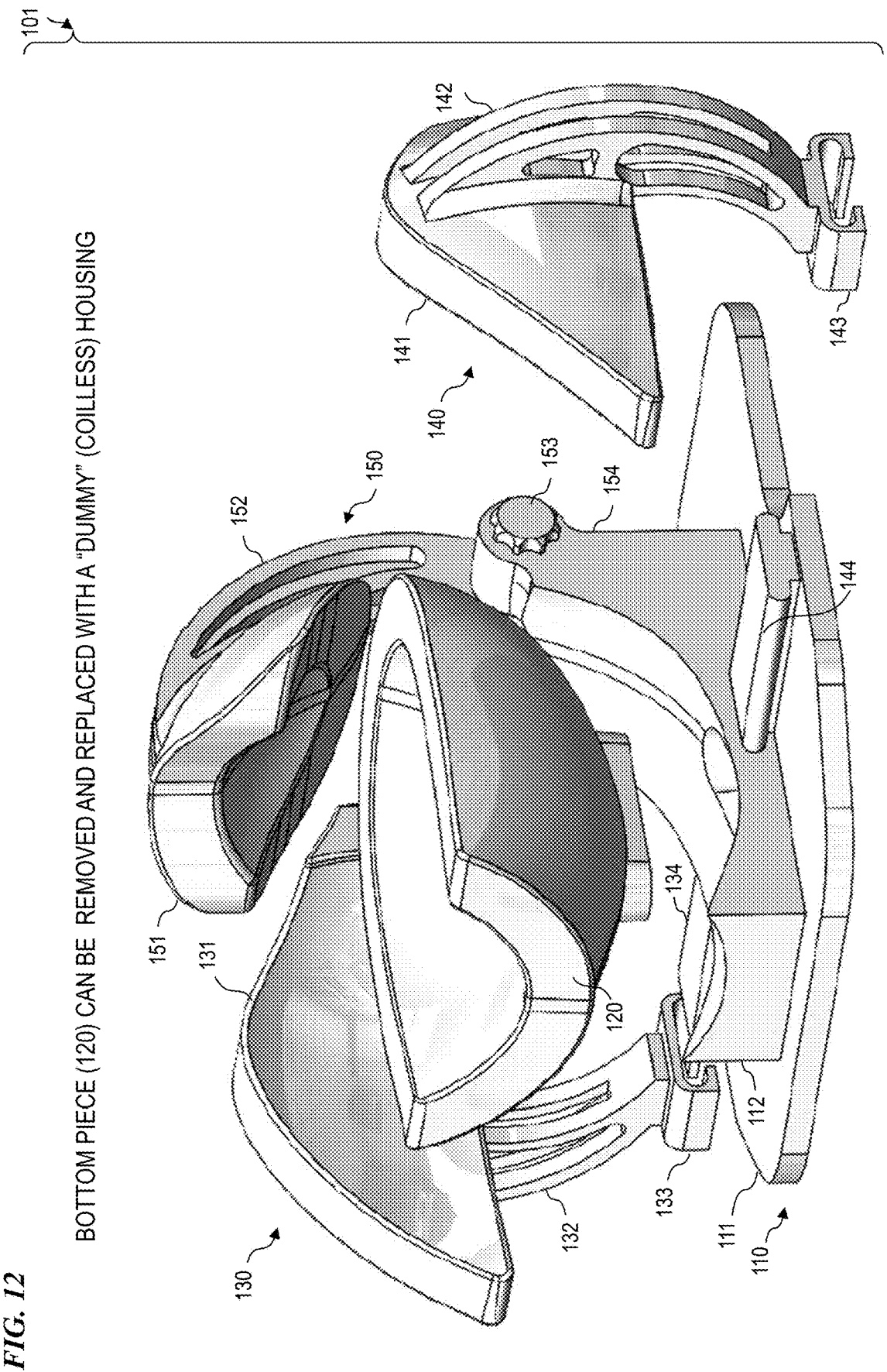
FIG. 12 is a perspective-view diagram of a head coil system 101 in an open position (from a different angle than that of FIG. 1), according to some embodiments of the present invention.

FIG. 12 is a perspective-view diagram of a head coil system 101 in an open position (from a different angle than that of FIG. 1), according to some embodiments of the present invention. As noted, in some embodiments, the total number of coils loops circuits 182-185 and their corresponding pluralities of tune-and-match preamplifier circuits 194 exceed the number of available channels in a given MRI machine, so some embodiments include "dummy" head parts (e.g., such that a coil-less bottom piece replaces the part 120 that includes coils and/or preamplifiers and the like) that are swapped in to replace unused coil loops (such as, e.g., the coil loops in part 120, which could be damaged if left unconnected in an operating MRI system and which can also cause undesirable loading and matching problems).

Figure 13:
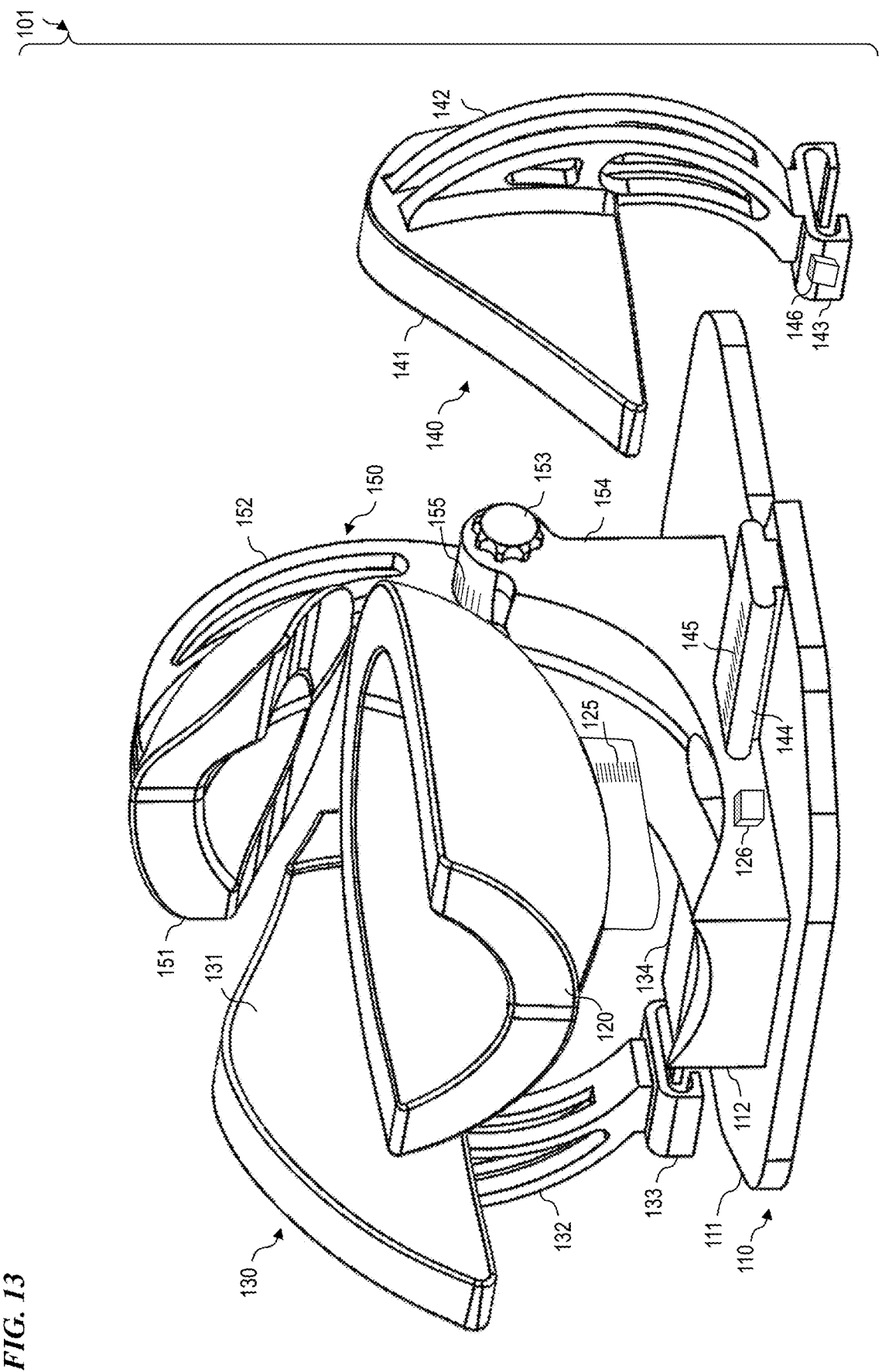
FIG. 13 is a perspective-view line diagram of a head coil system 101 in an open position (from the same angle than that of FIG. 12), according to some embodiments of the present invention.

FIG. 13 is a perspective-view line diagram of a head coil system 101 in an open position (from the same angle than that of FIG. 12), according to some embodiments of the present invention.

Figure 14:
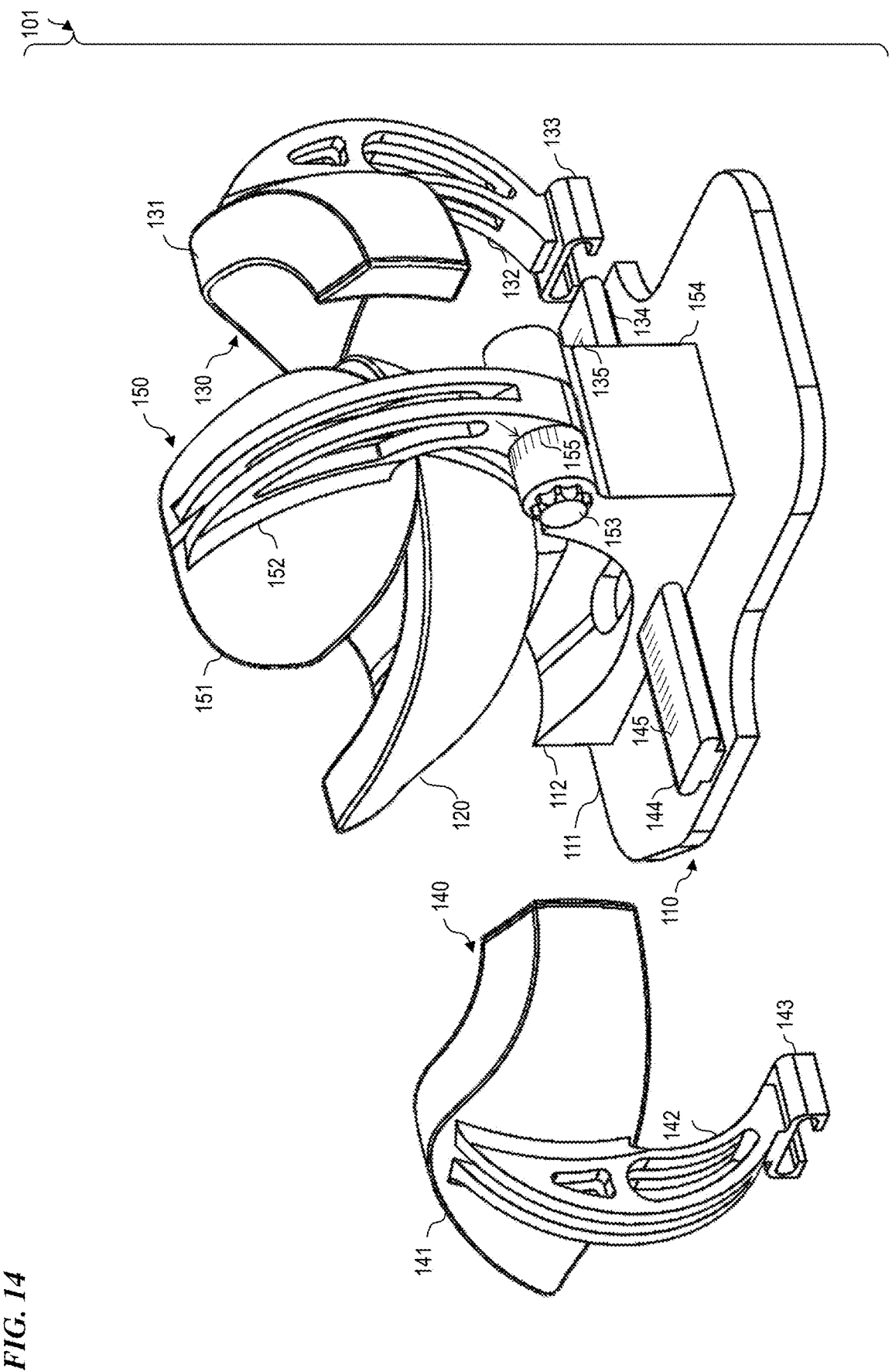
FIG. 14 is a perspective-view line diagram of a head coil system 101 in an open position (from a different angle than that of FIG. 12), according to some embodiments of the present invention.

FIG. 14 is a perspective-view line diagram of a head coil system 101 in an open position (from a different angle than that of FIG. 12), according to some embodiments of the present invention.

Figure 15:
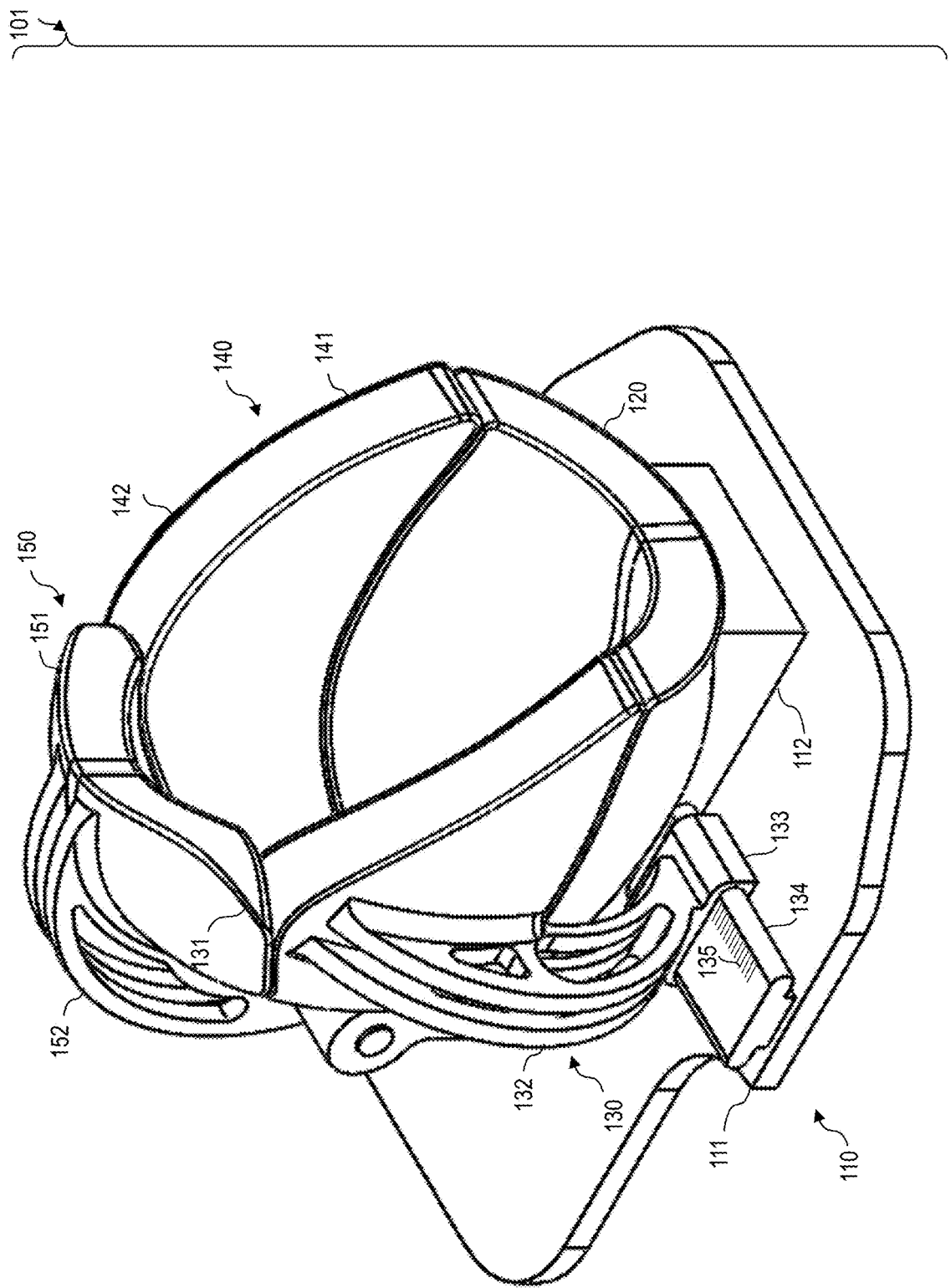
FIG. 15 is a perspective-view line diagram of a head coil system 101 in a closed position, according to some embodiments of the present invention.

FIG. 15 is a perspective-view line diagram of a head coil system 101 in a closed position, according to some embodiments of the present invention.

Figure 16:
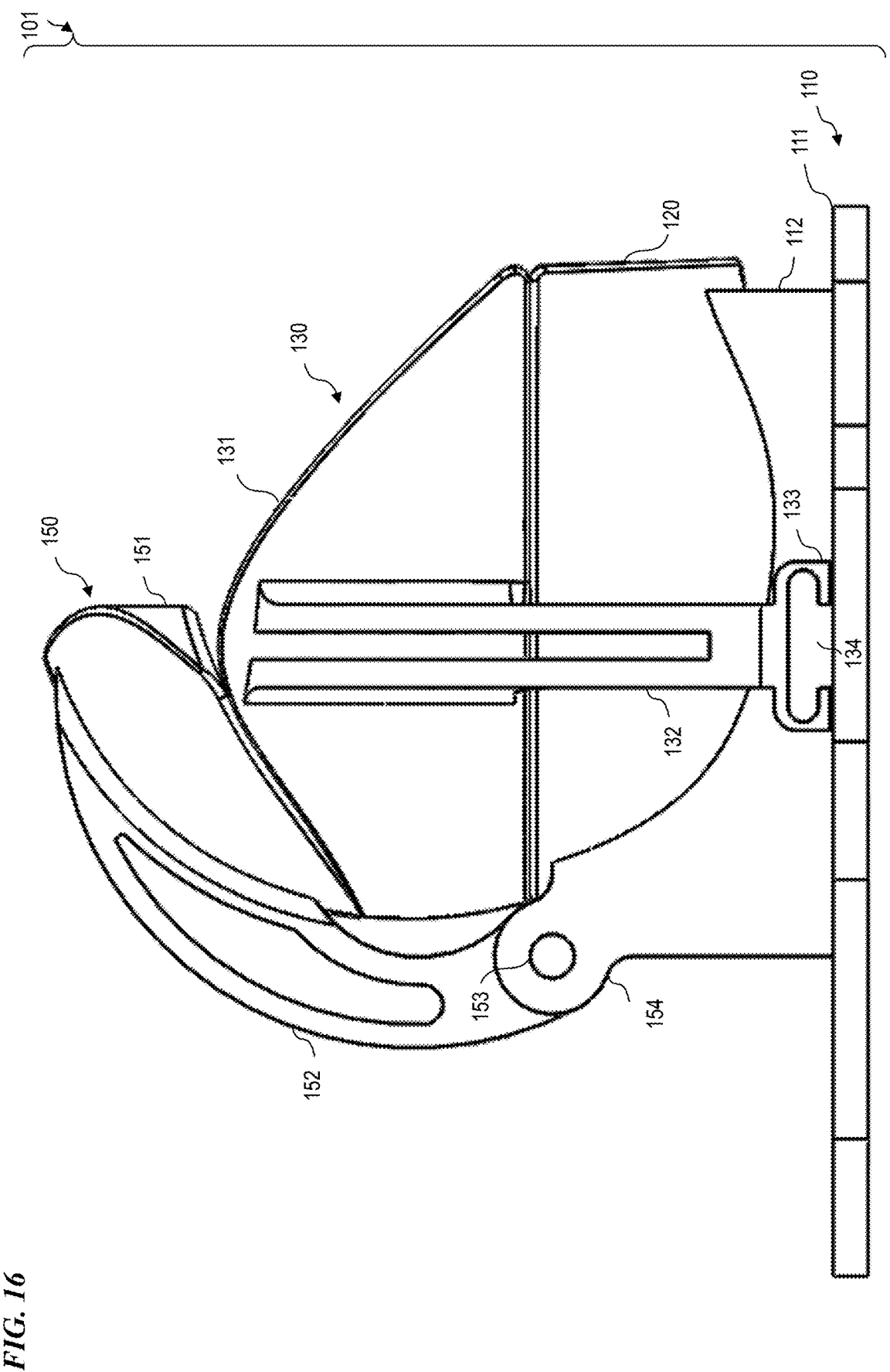
FIG. 16 is a side elevational-view line diagram of a head coil system 101 in a closed position, according to some embodiments of the present invention.

FIG. 16 is a side elevational-view line diagram of a head coil system 101 in a closed position, according to some embodiments of the present invention.

Figure 17:
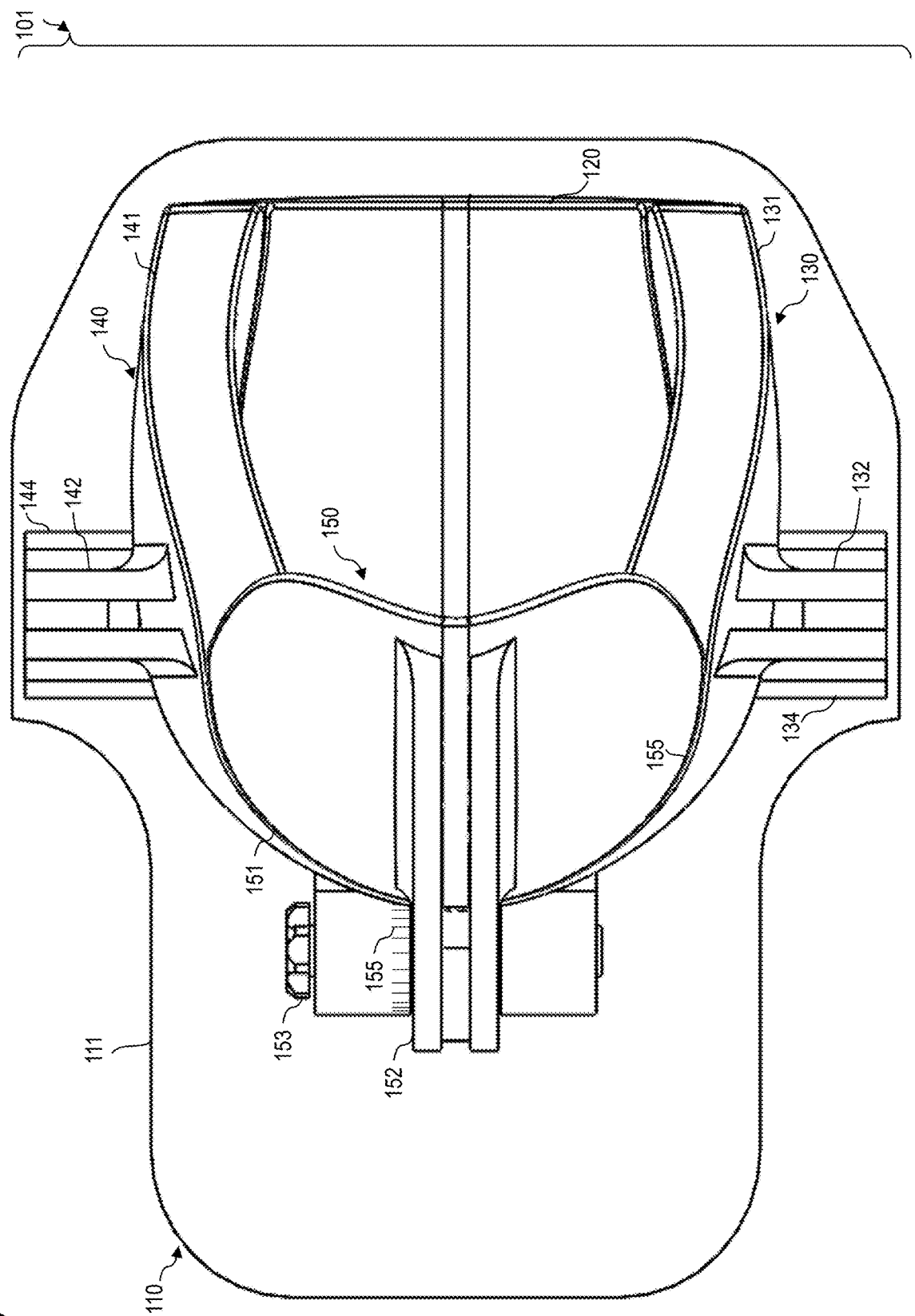
FIG. 17 is a front plan-view line diagram of a head coil system 101 in a closed position, according to some embodiments of the present invention.

FIG. 17 is a front plan-view line diagram of a head coil system 101 in a closed position, according to some embodiments of the present invention.

Figure 18A:
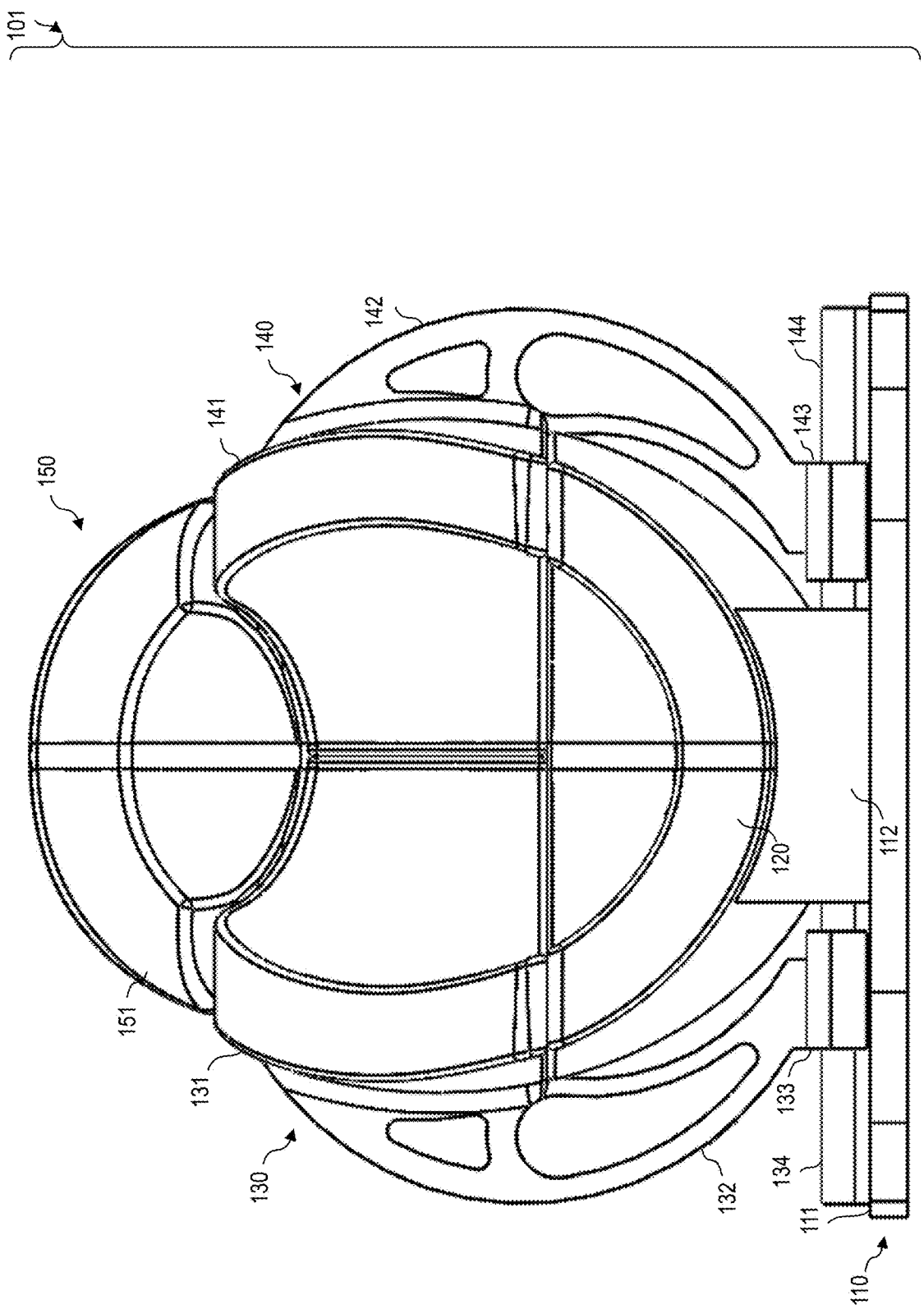
FIG. 18A is a bottom elevational-view line diagram of a head coil system 101 in a closed position, according to some embodiments of the present invention.

FIG. 18A is a bottom elevational-view (from-the-patient's-feet direction view) line diagram of a head coil system 101 in a closed position, according to some embodiments of the present invention.

Figure 18B:
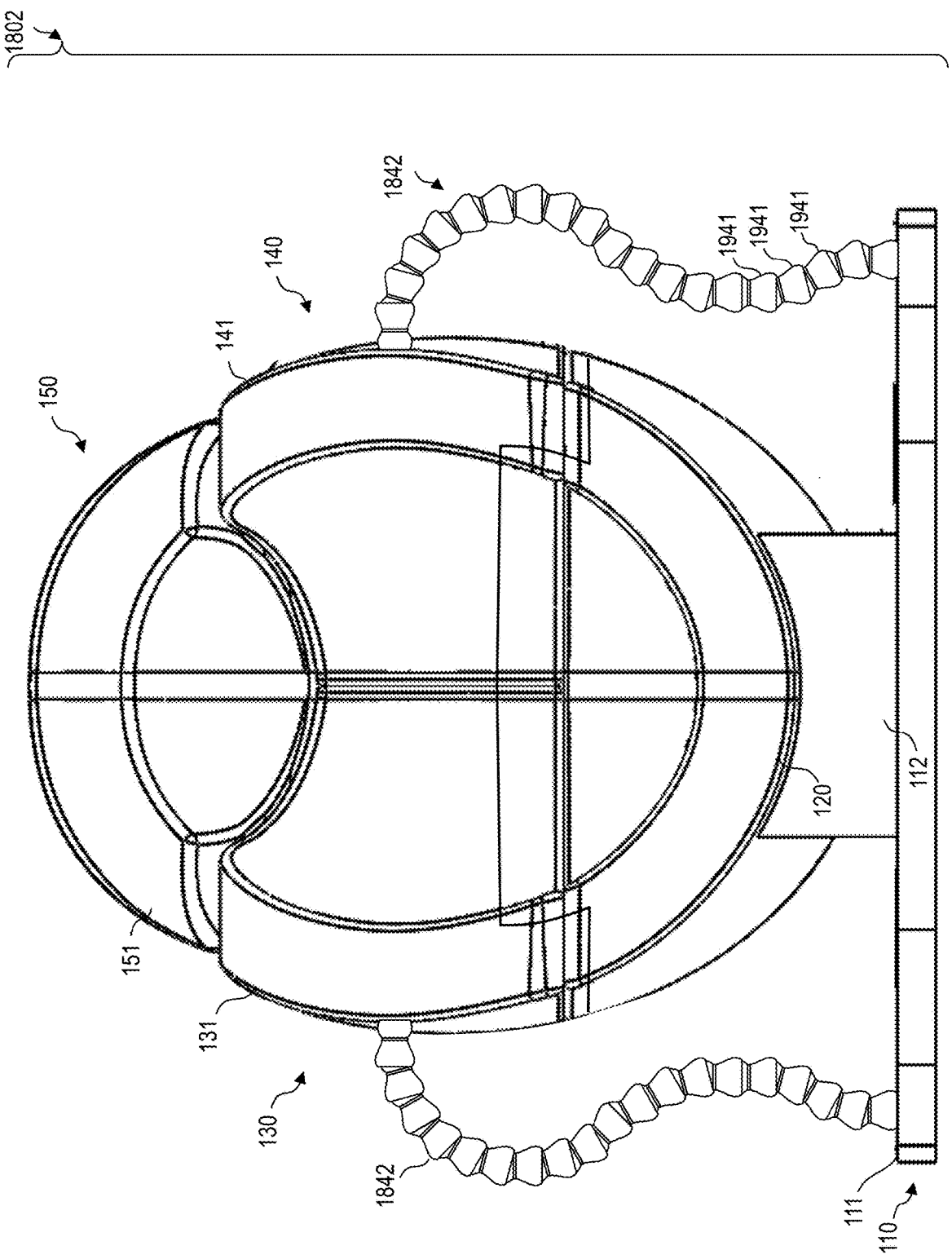
FIG. 18B is a bottom elevational-view line diagram of a head coil system 1802 in a closed position, according to some embodiments of the present invention.

FIG. 18B is a bottom elevational-view line diagram of a head coil system 1802 in a closed position, according to some embodiments of the present invention. In some embodiments, head coil system 1902, rather than slidable or hinged positioners, includes stiff bendable modular positioners 1842 (e.g., a plurality of modular pieces 1941 that are, in some embodiments, connected to the base unit 110) such as ½-inch or ¾-inch (about 12.7 mm-diameter or about 19-mm-diameter) LOC-LINE®-type modular hoses available from Lockwood Products (www.loc-line.com). LOC-LINE®-type bendable modular positioners 1842 are stiff enough to hold the location and orientation of the respective head-coil parts as manually set by the health-care professional. FIG. 21B shows a side elevational view of head coil system 1902.

Figure 19A:
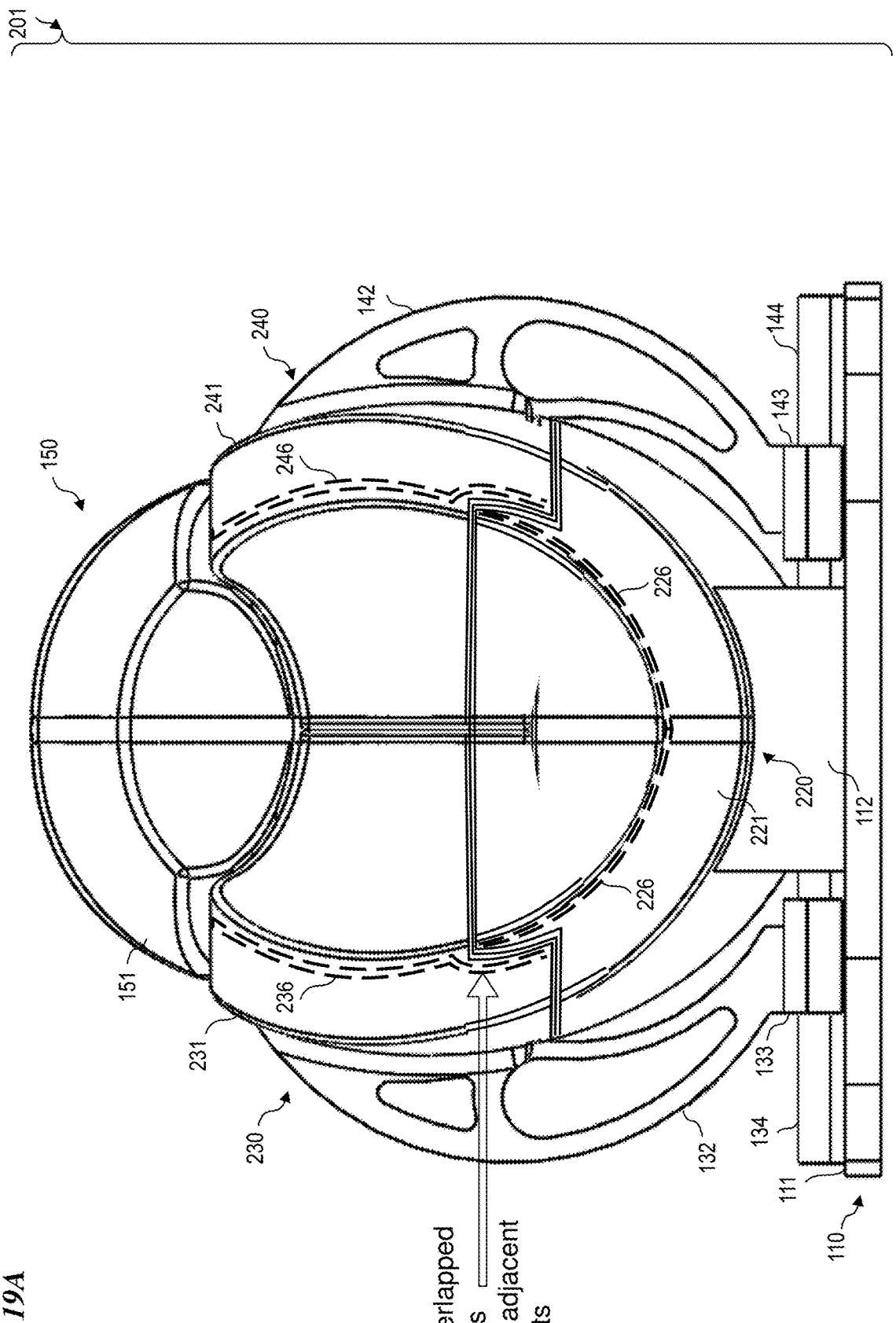
FIG. 19A is a bottom elevational-view line diagram of a head coil system 201 in a closed position, according to some embodiments of the present invention.

FIG. 19A is a bottom elevational-view (from-the-patient's-feet direction view) line diagram of a head coil system 201 in a closed position, according to some embodiments of the present invention. In some embodiments, system 201 is substantially similar to system 101, but differs in that back-of-head coil part 220 is shaped and its coil loops 226 are positioned so as to overlap corresponding coil loops 236 in right-side-of-head coil part 230, and corresponding coil loops 246 in left-side-of-head coil part 140. Accordingly, back-of-head coil 221 is shaped to overlap right-side-of-head coil 131 and left-side-of-head coil 141 at their respective adjacent edges, as shown.

Figure 19B:
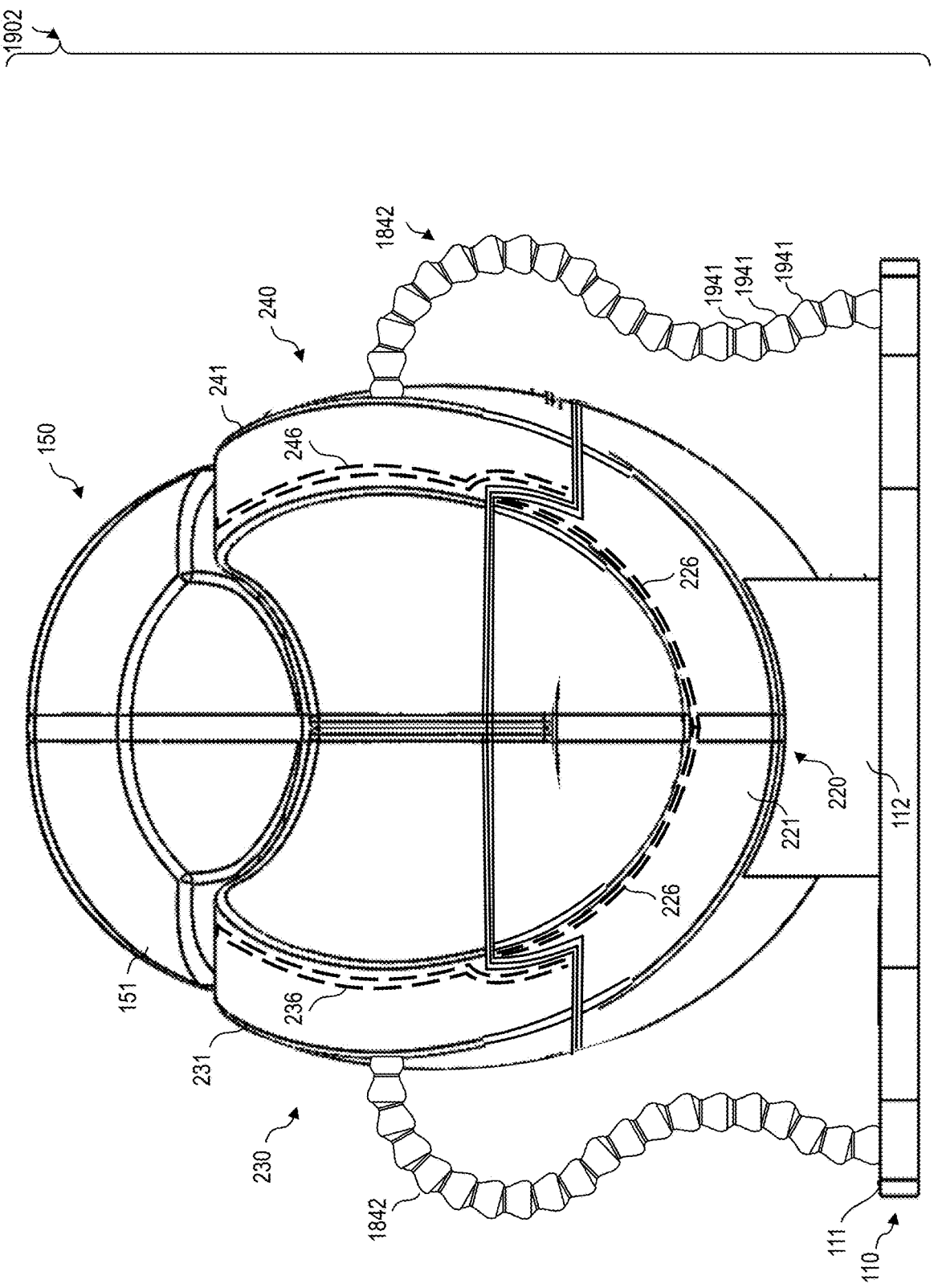
FIG. 19B is a bottom elevational-view line diagram of a head coil system 1902 in a closed position, according to some embodiments of the present invention.

FIG. 19B is a bottom elevational-view line diagram of a head coil system 1902 in a closed position, according to some embodiments of the present invention. In some embodiments, head coil system 1902 includes bendable modular positioners 1842 (e.g., a plurality of modular pieces 1941 that are, in some embodiments, connected to the base unit 110) such as ½-inch or ¾-inch (about 12.7 mm-diameter or about 19-mm-diameter) LOC-LINE®-type modular hoses available from Lockwood Products (www.loc-line.com). LOC-LINE®-type bendable modular positioners 1842 are stiff enough to hold the location and orientation of the respective head-coil parts as manually set by the health-care professional.

Figure 20:
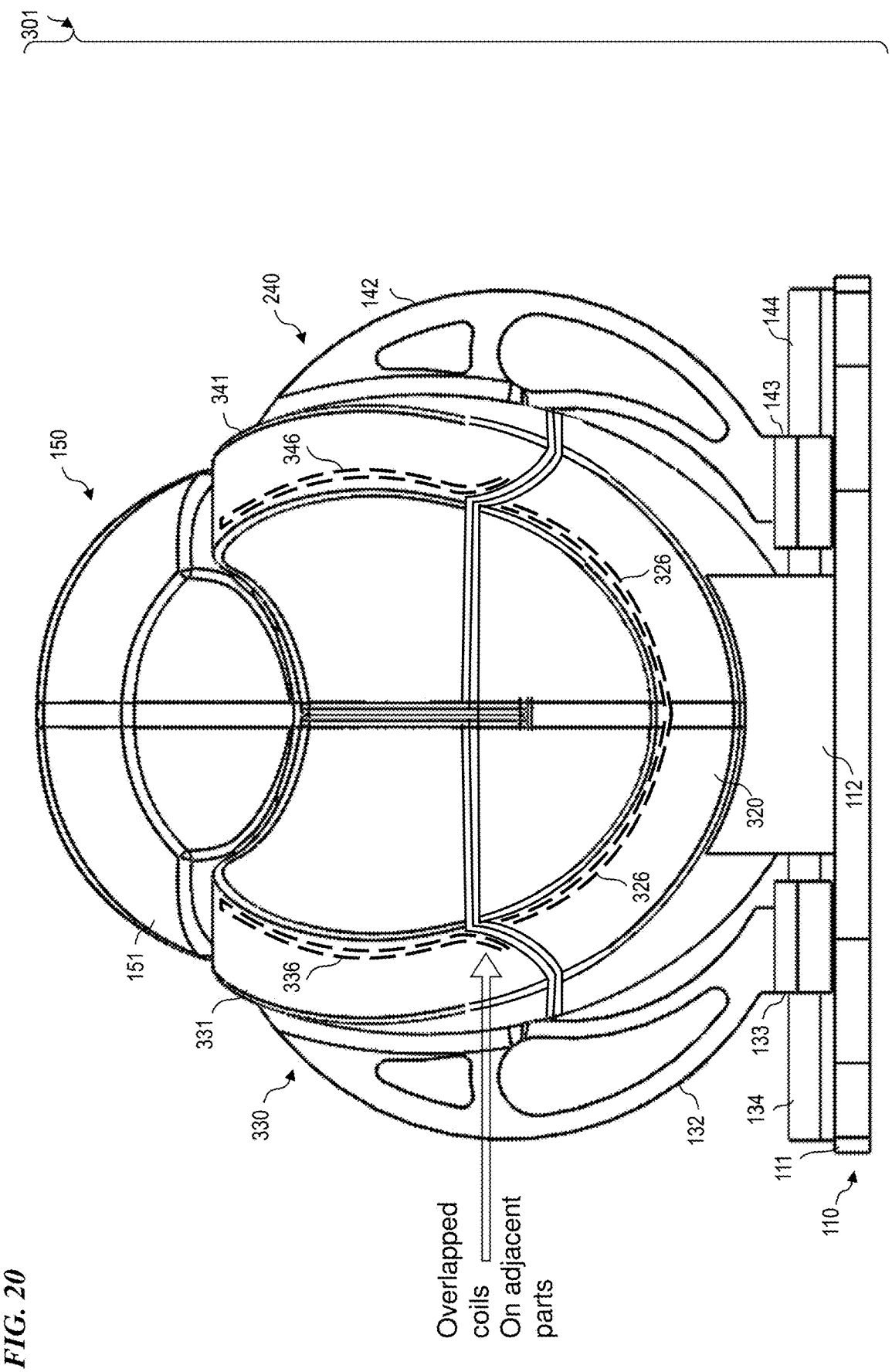
FIG. 20 is a bottom elevational-view line diagram of a head coil system 301 in a closed position, according to some embodiments of the present invention.

FIG. 20 is a bottom elevational-view (from-the-patient's-feet direction view) line diagram of a head coil system 301 in a closed position, according to some embodiments of the present invention. In some embodiments, system 301 is substantially similar to system 101, but differs in that back-of-head coil part 320 is shaped and its coil loops 326 are positioned so as to overlap corresponding coil loops 336 in right-side-of-head coil part 330, and corresponding coil loops 346 in left-side-of-head coil part 140. Accordingly, back-of-head coil 321 is shaped to overlap right-side-of-head coil 331 and left-side-of-head coil 341 at their respective adjacent edges, as shown.

Figure 21A:
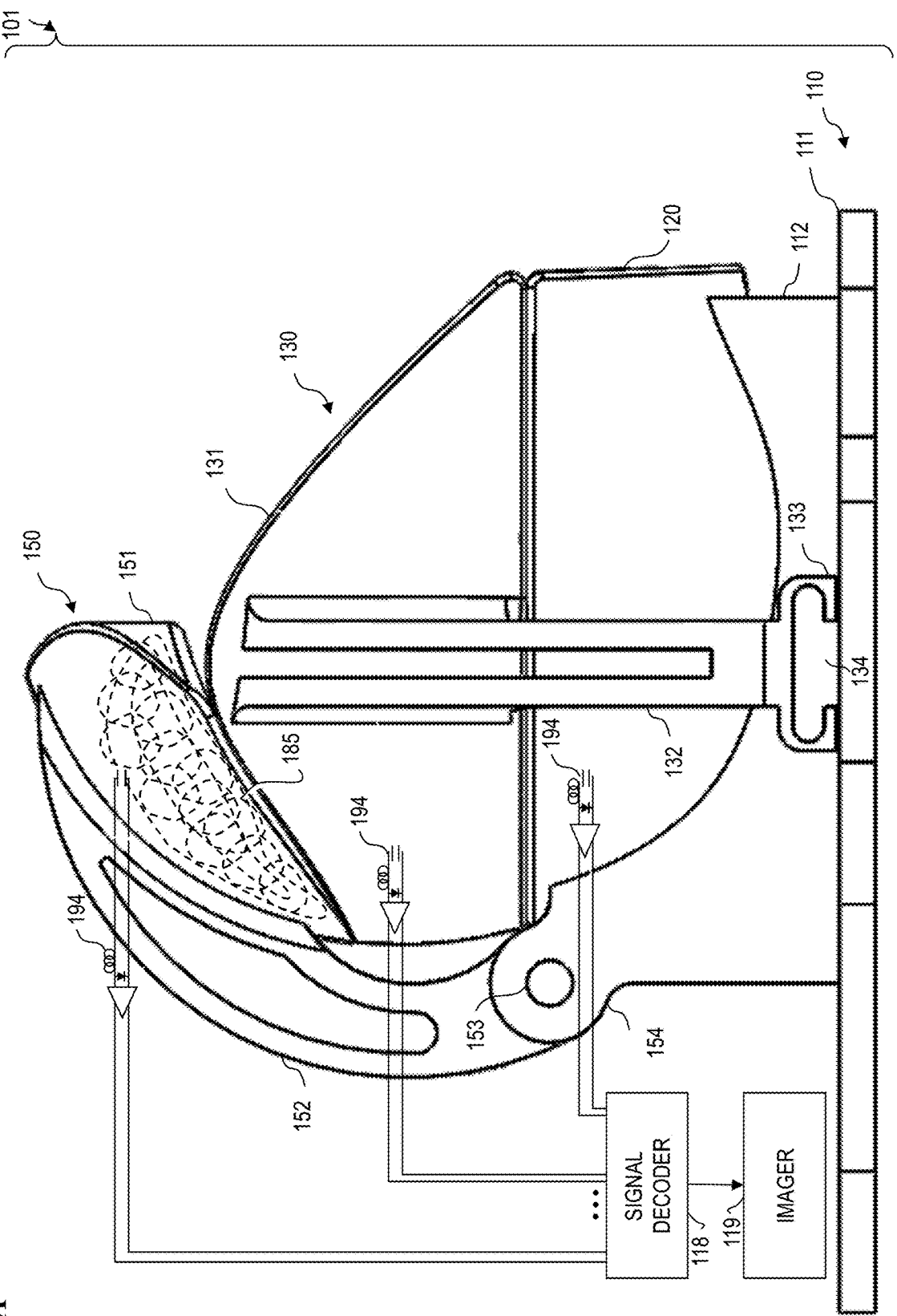
FIG. 21A is a side elevational-view line diagram of a head coil system 102 (as also shown in FIG. 2) in a closed position, according to some embodiments of the present invention.
Figure 21B:
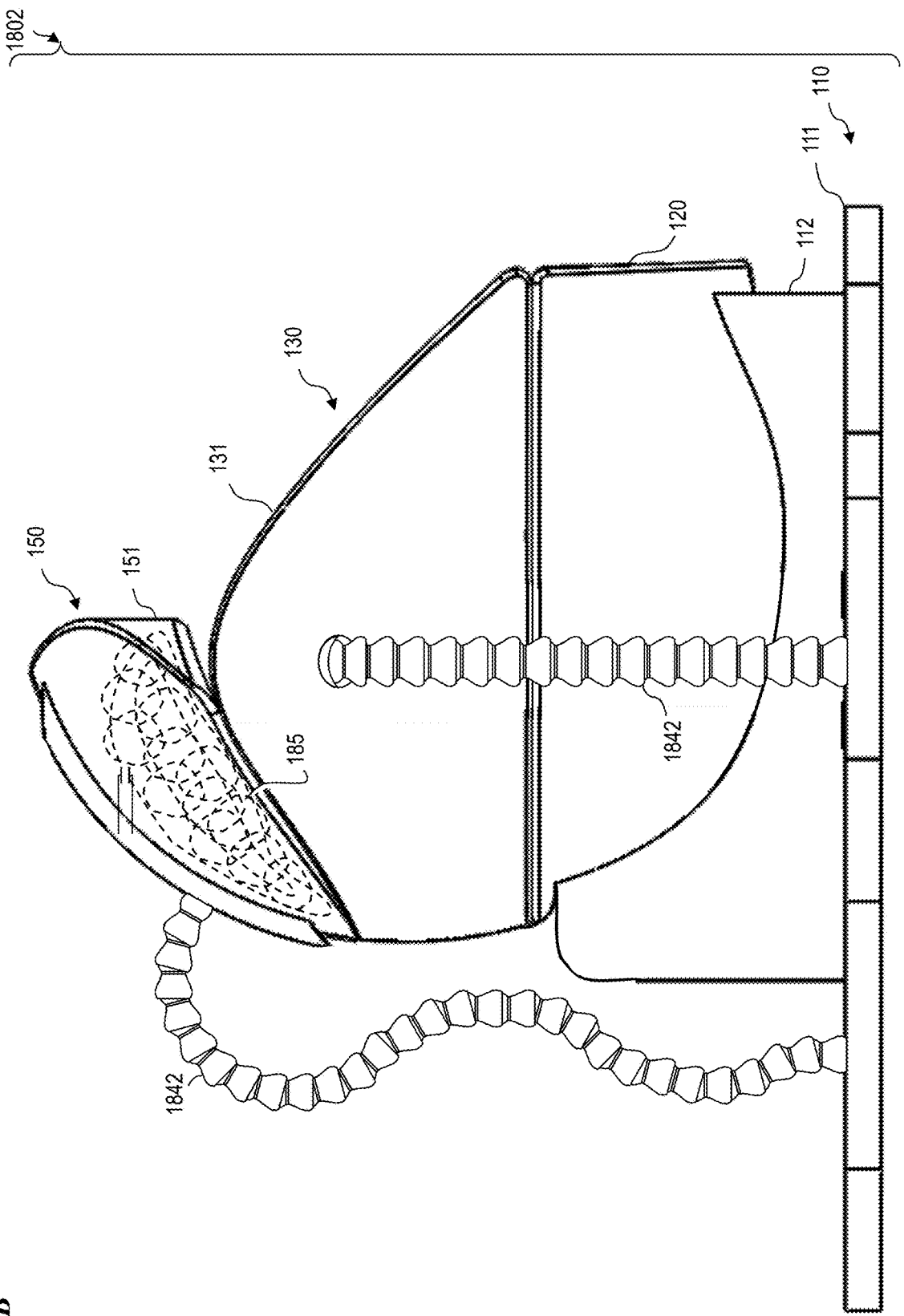
FIG. 21B is a side elevational-view line diagram of a head coil system 1802 (as shown in FIG. 19B) in a closed position, according to some embodiments of the present invention.

FIG. 21A is a side elevational-view line diagram of a head coil system 102 (as also shown in FIG. 2) in a closed position, according to some embodiments of the present invention. The various parts and features are as described for FIG. 2 above.

FIG. 21B is a bottom elevational-view line diagram of a head coil system 1902 in a closed position, according to some embodiments of the present invention. In some embodiments, head coil system 1902 includes bendable modular positioners 1842 (in some embodiments, e.g., connected to the base unit 110) such as ½-inch or ¾-inch (about 12.7 mm-diameter or about 19-mm-diameter) LOC-LINE® modular hoses available from Lockwood Products (www.loc-line.com). LOC-LINE®-type bendable modular positioners 1842 are stiff enough to hold the location and orientation of the respective head-coil parts as manually set by the health-care professional.

Figure 22:
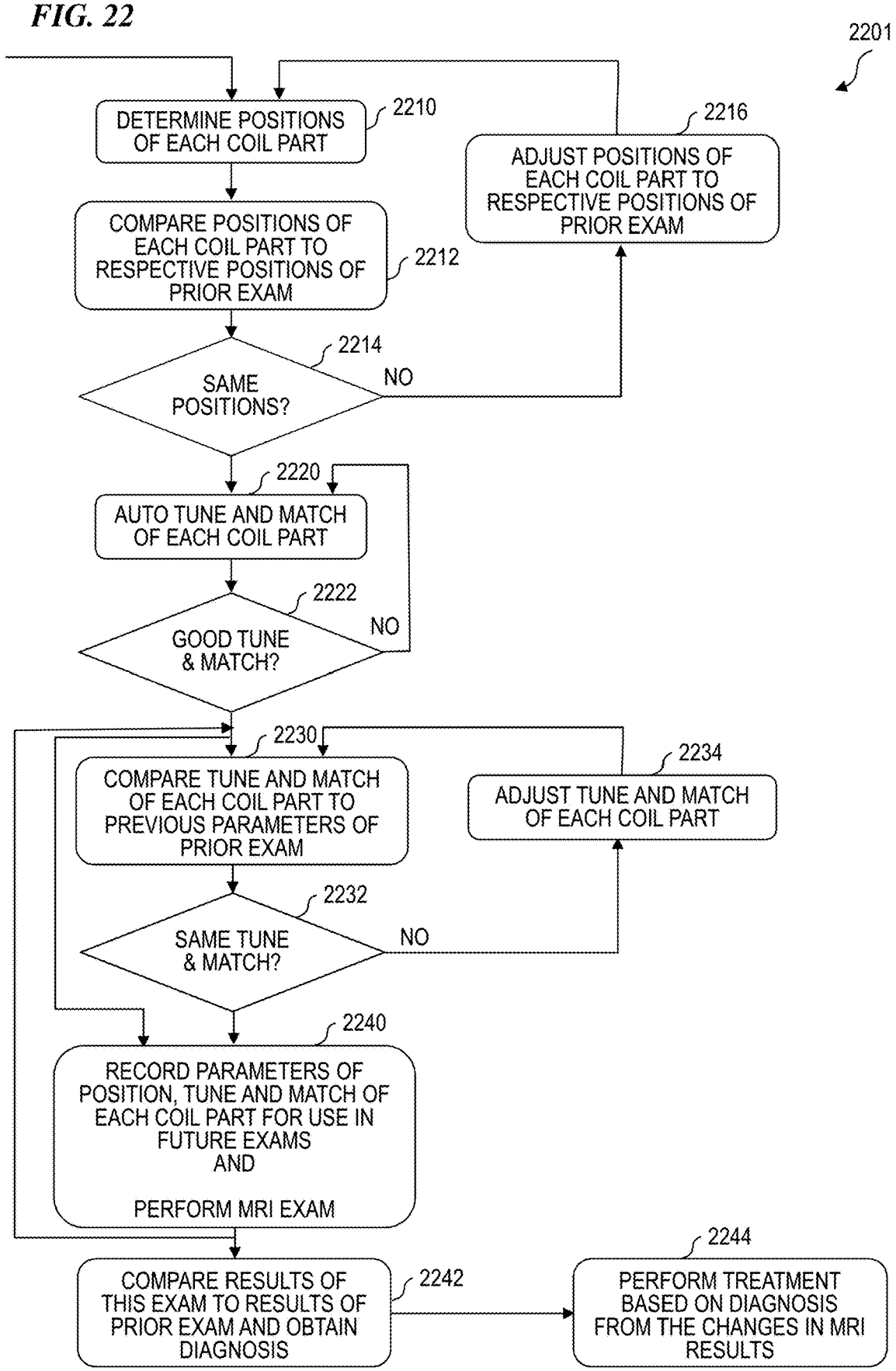
FIG. 22 is a flow chart of a head coil system and method 2201, according to some embodiments of the present invention.

FIG. 22 is a flow chart of a head coil system and method 2201, according to some embodiments of the present invention. In various embodiments, head coil system and method 2201 is implemented in hardware and/or software. In some embodiments, electrical and/or optical position and/or angle sensors are used detect and report the positions and angles of the various parts 120, 130, 140 and 150 to their desired positions and orientations relative to one another and relative to base 110. In some embodiments, mechanical actuators are provided along with the position/angle sensors to adjust the position and/or angle/orientation of the various parts 120, 130, 140 and 150 relative to one another and relative to base 110, in order to automatically obtain the same experimental positions for each of a plurality of exams performed at different times for a given patient. In some embodiments, at block 2210, the present invention determines the position and/or orientation of each of a plurality of the coils parts 120, 130, 140, and 150. If this particular patient has had a prior examination using this system, at block 2212 the present invention compares the positions of each coil part to their respective positions during the prior examination(s), and at block 2214 checks results of the compare, and if the positions are not the same (to within a desired and/or predetermined tolerance), then at block 2216, the system and method adjust positions of each coil part that was not in the correct position to more closely match respective positions of the part during the prior examination(s). In some embodiments, at block 2210, the present invention also determines the pressure of at least one of the coils parts 120, 130, 140, and 150 against the tissue of the patient, and at block 2216 the system and method also adjusts positions and/or orientations of each coil part that was not applying the correct pressure, reducing the pressure if too high, and increasing the pressure if the measurement was too low. In some embodiments, this allows the system and method of the present invention a break in the middle of an MRI imaging session. In some embodiments, the remote-control actuator coil-part positioners further include pressure sensors in one or more locations on the patient-facing side of the head-coil parts, and signals from the pressure sensors are used by the MRI health-care professional (or automatically by a computerized controller) to provide enough pressure to immobilize the patient's head without putting too much pressure that would injure the patient or make the patient unduly uncomfortable. In some embodiments, the adjustment of position/angle is done at least in part manually. In other embodiments, the adjustment of position/angle is done automatically using mechanical actuators under electronic and/or computer control. In some embodiments, at block 2220, the present invention performs an automatic tune and match operation to tune each of the coil loops to a desired predetermined frequency (tuning) and to a desired predetermined impedance (matching), and at block 2222 checks results of the tune-and-match, and if the results are not optimal (to within a desired and/or predetermined tolerance), then loops back to block 2220. In some embodiments, instead of or in addition to the operation of blocks 2220 and 2222, the system and method 2201 execute block 2230 to compare the tune-and-match results of each coil part to corresponding parameters of a prior examination, and at block 2232 determine whether the tune-and-match results are the same as those of the prior examination, and if not, go to block 2234 to adjust the tune and match for each coil part to the frequency and impedance parameters from the prior examination, in order to obtain the best match of experimental conditions. In some embodiments, at block 2240, the system and method record the parameters of positions, characteristic tune frequencies and characteristic match impedances (e.g., into a database or other computer storage, and correlated to this particular patient) for use in fully documenting the present examination conditions and for future examinations so those can be matched to the current conditions. The MRI examination is then performed and its results are stored. In some embodiments, after block 2240, the system and method loop back to block 2230 or block 2220 to readjust position, tune and match parameters to other values (perhaps to match a different prior examination, or to obtain a better tune and match) and that portion of the algorithm is repeated. In some embodiments, at block 2242, results of the current examination are compared to results from one or more prior examinations (in some embodiments, this is done automatically using a computerized algorithm, as are well known) and the comparison is used to determine a diagnosis of a condition of the patient, and at block 2244 a treatment is performed on the patient based on the diagnosis obtained at block 2242.

Figure 23:
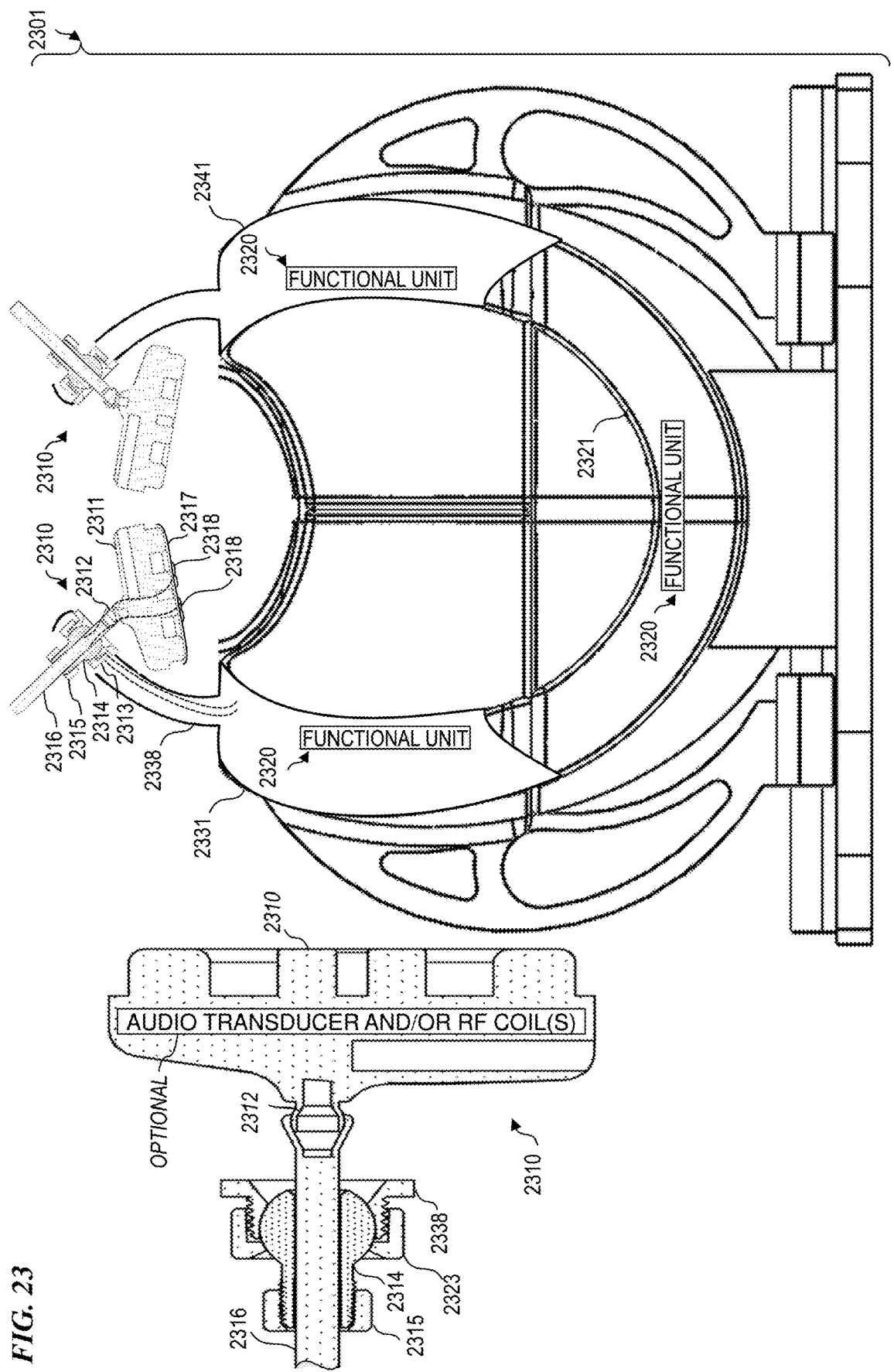
FIG. 23 is a bottom elevational-view line diagram of a head coil system 2301 in a closed position, according to some embodiments of the present invention.

Referring to FIG. 23, in some embodiments, one or more of the head coil units 120, 130, 140, and/or 150 includes a patient-interface positioner/stabilizer (such as described, for example, in United States Patent Publication 2015/0196226 by Tramm et al. titled "Method and positionable patient-interface apparatus for an MRI system," which is incorporated herein by reference) connected to a reference position on the respective head coil units 120, 130, 140, and/or 150, a first lockable joint on the positioner; and a patient interface connected to a patient-proximal end of the positioner by a second joint, wherein the first patient-interface is moveably positioned to a selected pitch angle, a selected yaw angle, and a selected one of a plurality of distances relative to the reference position on the frame. The first lockable joint is configured to be tightened to yieldably hold the first patient-interface at the selected pitch and yaw angles, and at the selected one of the plurality of distances, relative to the reference position. Optionally a second substantially similar patient-interface and assembly are provided. In some embodiments, the earpiece(s) optionally include audio transducer(s) and/or RF coil(s).

FIG. 23 is a bottom elevational-view line diagram of a head coil system 2301 in a closed position, according to some embodiments of the present invention. In some embodiments, right head-coil unit 2331 includes an extension frame 2338 to which an adjustable patient-interface positioner/stabilizer 2310 is attached. In some embodiments, a corresponding structure is applied to the left head-coil unit 2341. In some embodiments, extension frame 2338 is removably attachable to right head-coil unit 2331, wherein one includes a plug and the other includes a conforming socket, each optionally including electrical and/or optical connections for conveying signals between a functional unit in patient-interface positioner/stabilizer patient-contact piece 2311. In some embodiments, patient-interface positioner/stabilizer patient-contact piece 2311 is covered by a sterile disposable polymer film or fabric 2317 that touches the patient's skin. In some embodiments, sterile disposable polymer film or fabric 2317 further includes one or more patient-contact electrodes 2318 (e.g., made of a bio-compatible metal composition, conductive polymer, ionic gel and/or the like) connected to signal wires (and/or optical fibers) that are used for delivering stimulation signals or receiving sense signals. In some embodiments, patient-interface positioner/stabilizer patient-contact piece 2311 includes one or more other transducers such as haptic vibrators, audio transducers, or the like. In some embodiments, patient-interface positioner/stabilizer patient-contact piece 2311 includes a cushioned patient contact surface. In some embodiments, patient-interface positioner/stabilizer patient-contact piece 2311 is connected by ball joint 2312 to a rod 2316 that can be extended/retracted and yieldably locked in place by locking nut 2315 to hold the cushioned patient-contact piece 2311 so as to restrain the patient from moving during the examination, but which will yield and release if the patient were to panic or be forced to move. Some embodiments further include a ball joint 2314 that allows multiple angular adjustments and that can be yieldably locked in place by threaded locking nut 2313. This combination allows a gentle restraint to be applied to help the patient remain substantially motionless during the examination. In some embodiments (not shown), an adjustable patient-interface positioner/stabilizer 2310 is attached through a central portion of the right head-coil unit 2331 and/or left head-coil unit 2341.

In some embodiments, each unit 2310 is implemented as described in one or more embodiments described in United States Patent Publication 2015/0196226 by Tramm et al., titled "Method and positionable patient-interface apparatus for an MRI system," which is incorporated herein by reference.

In some embodiments, one or more additional functional units 2320 (such as audio output transducers, sensing and/or stimulating electrodes, haptic vibrators, scent or odor delivery units, liquid cooling or warming units, or the like) are provided in one or more of the plurality of coil units 2321, 2331, and 2341. In some embodiments, the functional units further include on-coil transmit amplifiers, circuitry for simultaneous transmit/receive (TX/RX), auto tune-and-match, and other functions such as described in U.S. Pat. Nos. 9,160,295, 8,674,695, 8,854,042, 8,299,681, 5,557,247, 5,744,957, 8,380,266, 8,193,809, 8,217,653, 6,822,448, 6,538,441, 6,534,983, 6,495,069, 6,593,744, 6,664,465, 6,605,775, and 4,885,539, United States Patent Publications 2007/0236490, 2013/0106416, 2015/0196226 and 2015/0323624, each of which is incorporated herein by reference.

In some embodiments, the coil loops and/or functional modules in the head-coil units support a plurality of different frequencies and/or multiple nuclei/frequencies. In some embodiments, the present invention provides multiples varieties of each module which can be interchanged on the base 111 for obtaining signals and images from various nuclei (different frequencies), as well as supporting dual and/or triple frequencies, each frequency being independently electrically tuned within each module, and iteratively tuned and impedance-matched relative to one another. In some embodiments, each of a plurality of such modules are swapped in and out and the device 101 then works over multiple field strengths, nuclei, frequencies, modes, and the like.

Also, in some embodiments, the head-coil units (and coil-less ("dummy") replacement units) are configured to be removed and put onto various bases 110, each having different mechanical shapes and/or mating configurations (e.g., displacement-adjustment only versus angle-adjustment only versus both angle-adjustment and displacement-adjustment) to allow combined use with other radiological systems, devices, suites (e.g., different vendor's MR systems or table tops, other radiological system tools (e.g., computed tomography (CT), X-Ray, positron-emission tomography (PET), and the like), as well as cooperative interoperability with surgical tables, patient training/prep rooms, etc.).

In some embodiments, the present invention provides an apparatus for receiving radio-frequency (RF) signals suitable for magnetic-resonance imaging (MRI) and/or magnetic-resonance spectroscopy (MRS) from radio-frequency (RF) coils that are overlapped and/or concentric, but optionally sized differently and/or located at different elevations (distances from the patient's tissue) in order to extract signal from otherwise cross-coupled coil loops and to improve signal-to-noise ratio (SNR) of the received signal. This apparatus includes a plurality of independently positionable substrates, each having a first major surface and a second major surface; a plurality of receiver-electronics units (e.g., RF preamplifiers) mounted on each substrate, wherein the plurality of receiver-electronics units on each substrate includes a first receiver-electronics unit and a second receiver-electronics unit, and wherein each one of the plurality of receiver-electronics units on each substrate generates a respective output signal; a plurality of RF receiver units (e.g., antenna-coil loops) affixed to each substrate, wherein the plurality of RF receiver units includes a first RF receiver unit having a first antenna loop that is connected to the first receiver-electronics unit and a second RF receiver unit having a second antenna loop that is connected to the respective receiver-electronics unit; and decoder electronics operatively coupled to receive the output signals from the plurality of RF receiver units and configured to remove common-mode signals from the output signals from the plurality of RF receiver units.

In some embodiments, each of the plurality of RF receiver units further includes: a frequency-tuning capacitor, an impedance-matching capacitor, an RF trap, and a preamplifier.

In some embodiments, each of the plurality of RF receiver units further includes: a least one frequency-tuning capacitor, a plurality of impedance-matching capacitors, a plurality of RF traps, and a plurality of preamplifiers.

In some embodiments, the present invention provides an apparatus for receiving radio-frequency (RF) signals suitable for magnetic-resonance imaging (MRI) and/or magnetic-resonance spectroscopy (MRS) from radio-frequency (RF) coils that are overlapped and/or concentric, but optionally sized differently and/or located at different elevations (distances from the patient's tissue) in order to extract signal from otherwise cross-coupled coil loops and to improve signal-to-noise ratio (SNR) of the received signal. The apparatus includes a substrate having a first major surface and a second major surface; a first plurality of receiver-electronics units mounted on the substrate, wherein the first plurality of receiver-electronics units includes a first receiver-electronics unit and a second receiver-electronics unit, and wherein each one of the first plurality of receiver-electronics units generates an output signal; a plurality of RF receiver units affixed to the substrate, wherein the plurality of RF receiver units includes a first RF receiver unit having a first antenna loop that is connected to the first receiver-electronics unit and a second RF receiver unit having a second antenna loop that is connected to the first receiver-electronics unit; and decoder electronics operatively coupled to receive the output signals from the plurality of RF receiver units and configured to remove common-mode signals from the output signals from the plurality of RF receiver units.

In some embodiments, each of the plurality of RF receiver units further includes a frequency-tuning capacitor, an impedance-matching capacitor, an RF trap, and a preamplifier.

In some embodiments, each of the plurality of RF receiver units further includes a least one frequency-tuning capacitor, a plurality of impedance-matching capacitors, a plurality of RF traps, and a plurality of preamplifiers.

In some embodiments, the first antenna loop is affixed to the first major surface of the substrate and the second antenna loop is affixed to the second major surface such that the first antenna loop overlaps the second antenna loop such that a line perpendicular to the first major surface and passing through a center point of the first antenna loop is laterally offset from a center point of the second antenna loop. In some such embodiments, the apparatus further includes a second plurality of receiver-electronics units mounted on the substrate, wherein the second plurality of receiver-electronics units includes a third receiver-electronics unit operatively coupled to receive signals from the first antenna loop and a fourth receiver-electronics unit operatively coupled to receive signals from the second antenna loop, and wherein each one of the first plurality of receiver-electronics units generates its respective output signal and each one of the second plurality of receiver-electronics units generates its respective output signal, and the respective output signals are combined and decoded by the decoder electronics.

In some embodiments, the first antenna loop is affixed to the first major surface of the substrate and the second antenna loop is affixed to the second major surface and centered over the first antenna loop such that a center point of the first antenna loop and a center point of the second antenna loop are both located on a single line perpendicular to the first major surface.

In some embodiments, the first antenna loop is affixed to the first major surface of the substrate and the second antenna loop is affixed to the second major surface and laterally offset from the first antenna loop such that a center point of the first antenna loop and a center point of the second antenna loop are each located on one of two spaced-apart lines perpendicular to the first major surface.

In some embodiments, the first antenna loop is affixed to the first major surface of the substrate and the second antenna loop is affixed to the first major surface and centered relative to the first antenna loop such that a center point of the first antenna loop and a center point of the second antenna loop are located within two millimeters from one another, and wherein the first antenna loop and the first antenna loop are substantially coplanar.

In some embodiments, the first antenna loop is affixed to the first major surface of the substrate and the second antenna loop is affixed to the first major surface and laterally offset relative to the first antenna loop, and wherein the first antenna loop and the first antenna loop are substantially coplanar and have sizes that differ by more than ten percent.

In some embodiments, the first antenna loop is affixed to the first major surface of the substrate and the second antenna loop is oriented such that a plane of the second antenna loop is at an angle of at least ten degrees from a plane of the first antenna loop and centered relative to the first antenna loop such that a center point of the first antenna loop and a center point of the second antenna loop are located within two millimeters from one another.

In some embodiments, the present invention provides a method for receiving radio-frequency (RF) signals suitable for magnetic-resonance imaging (MRI) and/or magnetic-resonance spectroscopy (MRS) from radio-frequency (RF) coils that are overlapped and/or concentric, but optionally sized differently and/or located at different elevations (distances from the patient's tissue) in order to extract signal from otherwise cross-coupled coil loops and to improve signal-to-noise ratio (SNR) of the received signal. This method includes providing a substrate, a plurality of receiver-electronics units mounted on the substrate, each generating an output signal, a plurality of RF receiver units affixed to the substrate, each one of the plurality of RF receiver units including an antenna loop having a resonance frequency and connected to at least one of the plurality of receiver-electronics units, and decoder electronics operatively coupled to the plurality of RF receiver units; receiving RF MRI signals with the antenna loops; pre-amplifying the received RF MRI signals to generate output signals; and removing common-mode signals from the output signals.

Some embodiments of the method further include automatically adjusting electrical parameters of the receiver-electronics units to adjust their resonance frequency.

Some embodiments of the method further include automatically adjusting electrical parameters of the receiver-electronics units to adjust the resonance frequency by moving a non-magnetic mechanical-movement device.

In some embodiments of the method, the receiver-electronics units each includes a plurality of pi networks arranged at different radial directions around a shielded RF cable.

In some embodiments, the present invention provides a method for receiving radio-frequency (RF) signals suitable for magnetic-resonance imaging (MRI) and/or magnetic-resonance spectroscopy (MRS) from radio-frequency (RF) coils that are overlapped and/or concentric, but optionally sized differently and/or located at different elevations (distances from the patient's tissue) in order to extract signal from otherwise cross-coupled coil loops and to improve signal-to-noise ratio (SNR) of the received signal. This method includes providing a substrate, a plurality of receiver-electronics units mounted on the substrate, each generating an output signal, and a plurality of RF receiver units affixed to the substrate, each one of the plurality of RF receiver units including an antenna loop having a resonance frequency and connected to at least one of the plurality of receiver-electronics units, and decoder electronics operatively coupled to the plurality of RF receiver units; receiving RF MRI signals with the antenna loops; pre-amplifying the received RF MRI signals to generate output signals; and removing common-mode signals from the output signals.

In some embodiments, the method further includes automatically adjusting electrical parameters of the receiver-electronics units to adjust their resonance frequency.

In some embodiments, the method further includes automatically adjusting electrical parameters of the receiver-electronics units to adjust the resonance frequency by moving a non-magnetic mechanical-movement device.

In some embodiments, the method further includes affixing the first antenna loop to the first major surface of the substrate; and affixing the second antenna loop to the second major surface such that the first antenna loop overlaps the second antenna loop such that a line perpendicular to the first major surface and passing through a center point of the first antenna loop is laterally offset from a center point of the second antenna loop. In some such embodiments, the method also further includes providing a second plurality of receiver-electronics units mounted on the substrate, wherein the second plurality of receiver-electronics units includes a third receiver-electronics unit and a fourth receiver-electronics unit; operatively coupling the third receiver-electronics to receive signals from the first antenna loop; operatively coupling the fourth receiver-electronics unit to receive signals from the second antenna loop; generating respective output signals from each one of the first plurality of receiver-electronics units and each one of the second plurality of receiver-electronics units; and combining and decoding the respective output signals to generate an MRI image.

In some embodiments, the method further includes affixing the first antenna loop to the first major surface of the substrate; and affixing the second antenna loop to the second major surface of the substrate centered over the first antenna loop such that a center point of the first antenna loop and a center point of the second antenna loop are both located on a single line perpendicular to the first major surface.

In some embodiments, the method further includes affixing first antenna loop to the first major surface of the substrate; and affixing the second antenna loop to the second major surface of the substrate laterally offset from the first antenna loop such that a center point of the first antenna loop and a center point of the second antenna loop are each located on one of two spaced-apart lines perpendicular to the first major surface.

In some embodiments, the method further includes affixing first antenna loop to the first major surface of the substrate; and affixing the second antenna loop to the first major surface centered relative to the first antenna loop such that a center point of the first antenna loop and a center point of the second antenna loop are located within two millimeters from one another, and wherein the first antenna loop and the first antenna loop are substantially coplanar and differing in circumference by at least ten percent.

In some embodiments, the method further includes affixing the first antenna loop to the first major surface of the substrate; and affixing the second antenna loop to the first major surface laterally offset relative to the first antenna loop, and wherein the first antenna loop and the first antenna loop are substantially coplanar and have circumference sizes that differ by at least ten percent.

In some embodiments, the method further includes affixing the first antenna loop to the first major surface of the substrate; and positioning the second antenna loop such that a plane of the second antenna loop is oriented at an angle of at least ten degrees from a plane of the first antenna loop and centered relative to the first antenna loop such that a center point of the first antenna loop and a center point of the second antenna loop are located within two millimeters from one another.

In some embodiments, the present invention provides a non-transitory computer-readable medium having instructions stored thereon for causing a suitably programmed information processor to execute a method that includes receiving RF MRI signals with a plurality of antenna loops mounted to a substrate; pre-amplifying the received RF MRI signals using a plurality of receiver-electronics units to generate output signals; and removing common-mode signals from the output signals. In some embodiments, the medium contains instructions such that the method further includes using a feedback signal operatively coupled to the programmable information-processing device to provide feedback control in order to maintain an electrical parameter of the plurality of receiver-electronics units. In some embodiments, the medium contains instructions such that the method further includes controlling resistance, inductance and capacitance (RLC) values of the plurality of receiver-electronics units.

In some embodiments, the present invention provides a non-transitory computer-readable medium having instructions stored thereon for causing a suitably programmed information processor to execute a method that includes: auto-controlling an electrical parameter of each of a plurality of receiver-electronics units that is mounted to a MRI receiver coil unit. In some embodiments, the medium contains instructions such that the method further includes using a feedback signal operatively coupled to the programmable information-processing device to provide feedback control in order to maintain the electrical parameter of the plurality of receiver-electronics units. In some embodiments, the medium contains instructions such that the method further includes controlling resistance, inductance and capacitance (RLC) values of the plurality of receiver-electronics units.

In some embodiments, the present invention provides a non-transitory computer-readable medium having instructions stored thereon for causing a suitably programmed information processor to execute a method that comprises: autocontrolling an electrical parameter of an LC circuit that is mounted to a case of a snap-on balun attached to a shielded RF cable that has a peripheral shield conductor and at least one inner conductor for carrying RF signals, wherein the LC circuit has a resonance frequency at a frequency of RF signals carried on the at least one inner conductor, wherein the case includes a piercing structure electrically connected to the LC circuit and configured to pierce and electrically connect the LC circuit to the shield conductor of the shielded RF cable.

In some embodiments of the computer-readable medium, the method further includes using a feedback signal operatively coupled to the programmable information-processing device to provide feedback control in order to maintain the electrical parameter of the LC circuit.

In some embodiments of the computer-readable medium, the method further includes controlling resistance, inductance and capacitance (RLC) values of the LC circuit.

In some embodiments, the present invention provides an apparatus for holding a patient's head during a magnetic-resonance procedure. This apparatus includes: a first base part (e.g., 110); a plurality of independently positionable head-coil substrates (e.g., 131, 141, 151), wherein each one of the plurality of independently positionable head-coil substrates has a respective head-coil positioner (e.g., 133&134, 143&144, 152&153&154) operably connected to the first base part; a plurality of RF preamplifiers (e.g., 161) mounted on each one of the plurality of independently positionable head-coil substrates, wherein the plurality of RF preamplifiers on each substrate includes a first RF preamplifier and a second RF preamplifier, and wherein each one of the plurality of RF preamplifiers on each substrate generates a respective output signal; a plurality of RF receiver units (e.g., 182, 183, 184, 185, 236, 246, 226, 336, 346, 326) affixed to each substrate, wherein the plurality of RF receiver units includes a first RF receiver unit having a first antenna loop that is connected to the first RF preamplifier and a second RF receiver unit having a second antenna loop that is connected to the second RF preamplifier; and, in some embodiments, decoder electronics (e.g., 118) operatively coupled to receive the respective output signals from the plurality of RF preamplifiers and configured to remove common-mode signals from the output signals from the plurality of RF preamplifiers, and, in some embodiments, an imager (e.g., 119) configured to generate an image from the decoded output signals. Some embodiments of this apparatus further include a plurality of clamping mechanisms operable to yieldably lock the plurality of independently positionable head-coil substrates in different ones of a plurality of various fixed substantially non-moving and repeatable locations and orientations relative to one another. Some embodiments of this apparatus further include a plurality of electrically controllable positioning mechanisms operable to move and yieldably lock the various head-coil substrates in different ones of a plurality of various fixed non-moving and repeatable locations and orientations relative to one another. Some embodiments of this apparatus further include a plurality of position sensors operable to determine locations and orientations of each of the plurality of independently positionable head-coil substrates relative to the first base unit. Some embodiments of this apparatus further include a plurality of pressure sensors, wherein each one of the plurality of pressure sensors is operable to determine a pressure between one of the plurality of independently positionable head-coil substrates and a tissue of a patient. In some embodiments of this apparatus, the first base unit includes at least a first guide track, and at least one respective head-coil substrate positioner includes a sliding bracket mounted on the first guide track. In some embodiments of this apparatus, at least one respective head-coil substrate positioner includes a rotatable clamping mechanism that is positionable to a plurality of angles. In some embodiments of this apparatus, at least one respective head-coil substrate positioner includes a LOC-LINE®-type modular hose.

In some embodiments, the present invention provides a method for holding a patient's head during a magnetic-resonance procedure. This method includes: providing a first base part; connecting a plurality of independently positionable head-coil substrates to the first base part using respective ones of a plurality of head-coil positioners, wherein each one of the plurality of independently positionable head-coil substrates includes a plurality of RF preamplifiers mounted thereon, wherein the plurality of RF preamplifiers on each substrate includes a first RF preamplifier and a second RF preamplifier, and wherein each one of the plurality of RF preamplifiers on each substrate generates a respective output signal based on at least one RF antenna loop; positioning each one of the plurality of independently positionable head-coil substrates against a tissue of the patient's head; and removing common-mode signals from the output signals from the plurality of RF preamplifiers. Some embodiments of this method further include yieldably locking each one of the plurality of independently positionable head-coil substrates in different ones of a plurality of various substantially non-moving and repeatable locations and orientations relative to the first base unit. Some embodiments of this method further include electrically controlling and electrically yieldably locking at least one of the plurality of independently positionable head-coil substrates in one of a plurality of various substantially non-moving and repeatable locations and orientations relative to the first base unit. Some embodiments of this method further include electrically sensing locations and orientations of at least one of the plurality of independently positionable head-coil substrates relative to the first base unit. Some embodiments of this method further include electrically sensing a pressure between at least one of the plurality of independently positionable head-coil substrates and a tissue of a patient. In some embodiments of this method, the first base unit includes at least a first guide track, and at least one respective head-coil substrate positioner includes a sliding bracket, and wherein the method further includes mounting the sliding bracket on the first guide track. In some embodiments of this method, at least one respective head-coil substrate positioner includes a rotatable clamping mechanism, and wherein the method further includes positioning the rotatable clamping mechanism to a selected one of a plurality of angles and clamping rotatable clamping mechanism at the selected angle. In some embodiments of this method, at least one respective head-coil substrate positioner includes a LOC-LINE®-type modular hose.

In some embodiments, the present invention provides an apparatus for holding a patient's head during a magnetic-resonance procedure. This apparatus includes: a first base part (e.g., 110); means for connecting (e.g., 133, 134, 143, 144, 152, 153, 154, 1842) a plurality of independently positionable head-coil substrates (e.g., 131, 141, 151), to the first base part and for positioning each one of the plurality of independently positionable head-coil substrates against a tissue of the patient's head. In some embodiments of this apparatus, the means for positioning further include means for yieldably locking (e.g., 126, 136, 146, 153) each one of the plurality of independently positionable head-coil substrates in different ones of a plurality of various substantially non-moving and repeatable locations (e.g., 125, 135, 145) and orientations (e.g., 155) relative to the first base unit. In some embodiments of this apparatus, the means for positioning further include means for electrically controlling and electrically yieldably locking at least one of the plurality of independently positionable head-coil substrates in one of a plurality of various substantially non-moving and repeatable locations and orientations relative to the first base unit. In some embodiments of this apparatus, the means for positioning further include means for electrically sensing locations and orientations of at least one of the plurality of independently positionable head-coil substrates relative to the first base unit. In some embodiments of this apparatus, the means for positioning further include means for electrically sensing a pressure between at least one of the plurality of independently positionable head-coil substrates and a tissue of a patient.

In some embodiments of this apparatus, the first base unit includes at least a first guide track, and wherein the means for positioning includes a sliding bracket mounted on the first guide track.

In some embodiments of this apparatus, the means for positioning includes a rotatable clamping mechanism operably connected to the first base unit to a selected one of a plurality of angles and clamped at the selected angle.

In some embodiments of this apparatus, the means for positioning includes at least one respective head-coil substrate positioner that includes a LOC-LINE®-type modular hose.

In some embodiments of this apparatus, each one of the plurality of independently positionable head-coil substrates generates RF signals from a plurality of RF antenna loops, the apparatus further comprising means for removing common-mode signals from the output signals from the plurality of RF preamplifiers.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first, " "second," and "third," etc., are used merely as labels, and are not intended to impose numerical requirements on their objects.

What is claimed is:

1. An apparatus for holding a patient's head during a magnetic-resonance procedure, the apparatus comprising:
    a first base part;
    a plurality of independently positionable head-coil substrates, wherein each one of the plurality of independently positionable head-coil substrates has a respective head-coil positioner operably connected to the first base part, wherein the first base part includes at least a first guide track, and at least one of the respective head-coil positioners includes a sliding bracket mounted on the first guide track, wherein, when the patient's head is in position on the apparatus for the magnetic-resonance procedure, the at least one of the respective head-coil positioners is configured to move in a linear direction toward and away from the patient's head while maintaining a loop overlap amount for all loop overlaps associated with the at least one respective head-coil positioner;

a plurality of radio-frequency (RF) preamplifiers mounted on each one of the plurality of independently positionable head-coil substrates, wherein the plurality of RF preamplifiers on each of the substrates includes a first RF preamplifier and a second RF preamplifier, and wherein each one of the plurality of RF preamplifiers on each of the substrates generates a respective analog output signal;

a plurality of RF receiver units affixed to each of the substrates, wherein the plurality of RF receiver units includes a first RF receiver unit having a first antenna loop that is connected to the first RF preamplifier and a second RF receiver unit having a second antenna loop that is connected to the second RF preamplifier;

decoder electronics operatively coupled to receive the respective analog output signals from the plurality of RF preamplifiers and configured to decode the respective analog output signals and configured to phase shift the respective analog output signals and adjust an amplitude of the respective analog output signals and to add the phase-shifted-and-amplitude-adjusted respective analog output signals to one another to improve signal-to-noise ratio (SNR); and a plurality of clamping mechanisms operable to yieldably lock the plurality of independently positionable head-coil substrates in different ones of a plurality of various fixed substantially non-moving and repeatable locations and orientations relative to one another, wherein the repeatable locations and orientations are indicated by indicia on the plurality of clamping mechanisms.

2. The apparatus of claim 1, further comprising a plurality of electrically controllable positioning mechanisms operable to move and yieldably lock the various head-coil substrates in different ones of a plurality of various fixed non-moving and repeatable locations and orientations relative to one another.

3. The apparatus of claim 1, further comprising a plurality of position sensors operable to determine locations and orientations of each of the plurality of independently positionable head-coil substrates relative to the first base part.

4. The apparatus of claim 1, further comprising a plurality of pressure sensors, wherein each one of the plurality of pressure sensors is operable to determine a pressure between one of the plurality of independently positionable head-coil substrates and a tissue of the patient.

5. The apparatus of claim 1, wherein at least one of the respective head-coil positioners includes a rotatable clamping mechanism that is positionable to a plurality of angles.

6. The apparatus of claim 1, wherein at least one of the respective head-coil positioners includes a bendable modular hose.

7. The apparatus of claim 1, further comprising an adjustable patient-interface positioner/stabilizer configured to hold a patient-interface positioner/stabilizer patient-contact piece against the patient to yieldably restrain the patient from moving during an examination, wherein the patient-interface positioner/stabilizer patient-contact piece includes at least one audio transducer.

8. The apparatus of claim 1, further comprising an adjustable patient-interface positioner/stabilizer configured to hold a patient-interface positioner/stabilizer patient-contact piece against the patient to yieldably restrain the patient from moving during an examination, wherein the patient-interface positioner/stabilizer patient-contact piece includes at least one haptic vibrator transducer.

9. The apparatus of claim 1, further comprising an adjustable patient-interface positioner/stabilizer configured to hold a patient-interface positioner/stabilizer patient-contact piece against the patient to yieldably restrain the patient from moving during an examination, wherein the patient-interface positioner/stabilizer patient-contact piece includes at least one haptic vibrator transducer, at least one audio transducer, and ascent-delivery unit.

10. The apparatus of claim 9, wherein the adjustable patient-interface positioner/stabilizer includes an extendable rod coupled to the patient-interface positioner/stabilizer patient-contact piece via a ball joint, and wherein the rod is locked in place via a locking nut.

11. A method for holding a patient's head during a magnetic-resonance procedure, the method comprising:

providing a first base part;

connecting a plurality of independently positionable head-coil substrates to the first base part using respective ones of a plurality of head-coil positioners, wherein the first base part includes at least a first guide track, and at least one of the respective head-coil positioners includes a sliding bracket mounted on the first guide track, wherein, when the patient's head is in position for the magnetic-resonance procedure, the at least one of the respective head-coil positioners moves in a linear direction toward and away from the patient's head while maintaining a loop overlap amount for all loop overlaps associated with the at least one respective head-coil positioner, wherein each one of the plurality of independently positionable head-coil substrates includes a plurality of radio-frequency (RF) preamplifiers mounted thereon, wherein the plurality of RF preamplifiers on each of the substrates includes a first RF preamplifier and a second RF preamplifier, and wherein each one of the plurality of RF preamplifiers on each of the substrates generates a respective analog output signal based on at least one RF antenna loop;

positioning each one of the plurality of independently positionable head-coil substrates against a tissue of the patient's head using the respective head-coil positioners;

decoding the respective analog output signals from the plurality of RF preamplifiers, phase shifting the respective analog output signals and adjusting an amplitude of the respective analog output signals, and adding the phase-shifted-and-amplitude-adjusted respective analog output signals to one another by decoder circuitry to improve signal-to-noise ratio (SNR);

providing a plurality of clamping mechanisms; and yieldably locking each one of the plurality of independently positionable head-coil substrates in different ones of a plurality of various substantially non-moving and repeatable locations and orientations relative to the first base part using the plurality of clamping mechanisms, wherein the repeatable locations and orientations are indicated by indicia on the plurality of clamping mechanisms.

12. The method of claim 11, further comprising electrically controlling and electrically yieldably locking at least one of the plurality of independently positionable head-coil substrates in one of a plurality of various substantially non-moving and repeatable locations and orientations relative to the first base part.

13. The method of claim 11, further comprising electrically sensing locations and orientations of at least one of the plurality of independently positionable head-coil substrates relative to the first base part.

14. The method of claim 11, further comprising electrically sensing a pressure between at least one of the plurality of independently positionable head-coil substrates and the tissue of the patient's head.

15. The method of claim 11, wherein at least one of the plurality of clamping mechanisms includes a rotatable clamping mechanism, and wherein the method further includes positioning the rotatable clamping mechanism of the plurality of clamping mechanisms to a selected one of a plurality of angles and clamping the rotatable clamping mechanism at the selected angle.

16. The method of claim 11, wherein at least one of the plurality of head-coil positioners includes a bendable modular hose.

17. An apparatus for holding a patient's head during a magnetic-resonance procedure, the apparatus comprising:
a first base part;
means for connecting a plurality of independently positionable head-coil substrates to the first base part, wherein the first base part includes at least a first guide track, wherein each one of the plurality of independently positionable head-coil substrates has a plurality of radio-frequency (RF) preamplifiers mounted thereon, and wherein each one of the plurality of RF preamplifiers on each of the substrates generates a respective analog output signal;
means for positioning each one of the plurality of independently positionable head-coil substrates against a tissue of the patient's head, wherein the means for positioning includes a sliding bracket mounted on the first guide track, and wherein, when the patient's head is in position on the apparatus for the magnetic-resonance procedure, the means for positioning is configured to move in a linear direction toward and away from the patient's head while maintaining a loop overlap amount for all loop overlaps associated with the means for positioning;
means for receiving the respective output analog signals from the plurality of RF preamplifiers, and for decoding the respective analog output signals, and for phase shifting the respective analog output signals and adjusting an amplitude of the respective analog output signals to obtain resulting signals, and for adding the phase-shifted-and-amplitude-adjusted respective output analog signals to one another to improve signal-to-noise ratio (SNR); and
wherein the means for positioning further includes means for yieldably locking each one of the plurality of independently positionable head-coil substrates in different ones of a plurality of various substantially non-moving and repeatable locations and orientations relative to the first base part, wherein the repeatable locations and orientations are indicated by indicia on the means for yieldably locking.

18. The apparatus of claim 17, wherein the means for positioning further comprises means for electrically controlling and electrically yieldably locking at least one of the plurality of independently positionable head-coil substrates in one of a plurality of various substantially non-moving and repeatable locations and orientations relative to the first base part.

19. The apparatus of claim 17, wherein the means for positioning further comprises means for electrically sensing locations and orientations of at least one of the plurality of independently positionable head-coil substrates relative to the first base part.

20. The apparatus of claim 17, wherein the means for positioning each one of the plurality of independently positionable head-coil substrates includes a bendable modular hose.

* * * * *